(12) United States Patent
King

(10) Patent No.: US 6,270,763 B1
(45) Date of Patent: Aug. 7, 2001

(54) CLONING AND RECOMBINANT PRODUCTION OF VESPID VENUM PHOSPHOLIPASES, AND IMMUNOLOGICAL THERAPIES BASED THEREON

(76) Inventor: Te Piao King, 340 E. 64th St., New York, NY (US) 10021

( * ) Notice: Subject to any disclaimer, the term of this patent is extended or adjusted under 35 U.S.C. 154(b) by 0 days.

(21) Appl. No.: 08/485,388

(22) Filed: Jun. 7, 1995

Related U.S. Application Data

(62) Division of application No. 08/385,745, filed on Feb. 8, 1995, now Pat. No. 5,612,209, which is a continuation of application No. 08/031,400, filed on Mar. 11, 1993, now abandoned.

(51) Int. Cl.⁷ .............................. A61K 38/46; C12N 9/20; C12N 1/20; C07H 21/04
(52) U.S. Cl. .................... 424/94.6; 435/198; 435/252.3; 435/252.33; 435/320.1; 536/23.1; 536/23.2; 536/23.5; 530/350
(58) Field of Search ........................ 424/94.6; 435/198, 435/252.3, 252.33, 320.1; 536/23.1, 23.2, 23.5; 530/350

(56) References Cited

U.S. PATENT DOCUMENTS

| | | | |
|---|---|---|---|
| 4,469,677 | 9/1984 | Michael et al. | 424/276 |
| 4,822,608 | 4/1989 | Benton et al. | 424/539 |
| 5,532,142 | * 7/1996 | Johnston et al. | 435/69.1 |

FOREIGN PATENT DOCUMENTS

WO 92/03551    3/1992   (WO) .

OTHER PUBLICATIONS

King et al. J. Allergy Clin. Immunol., 75 : 621–28, 1985.*
Gmachl et al. (1993) Proc. Natl. Acad. Sci. USA 90:3569–73.
Gmachl et al. (1993) FEBS Lett. 336:545–8.
Lu et al. (1993) *J. Allergy Clin. Immunol.,* 93:224(#367).
Soldatova, 1993, *J. Allergy Clin. Immunol.,* 93:283(#568).
King et al., 1993, *J. Allergy Clin. Immunol.,* 91:283(#569).
Lu et al. (1993) J. Immunol. 150:2823–30.
Soldatova (1993) FEBS Letters 320:145–9.
Dhillon et al., *J. Allergy Clin. Immunol.,* 90:42–51 1992.
Dhillon et al. (1992) *J. Allergy Clin. Immunol.,* 89:174 (#119).
Gaur et al., *Science,* 259:1491–1494 1992.
Griffith et al., *Gene.,* 113:263 1992.
Jacobson et al. (1992) *J. Allergy Clin. Immunol.,* 89:292(#591).
Scheiner (1992) Int. Arch. Allerg. Immunol. 98:93–6.
Valenta et al., *J. Exp. Med.,* 175:377, 1992.
Ales–Martinez et al., *Immunol. Today,* 12:201, 1991.
Fehlner et al., *J. Immunol.,* 146:799, 1991.
Gammon et al., *Immunol. Today.,* 12:193, 1991.
Griffith et al., *Int. Arch. Allergy Appl. Immunol.,* 96:296, 1991.
Han et al., *J. Allergy Clin. Immunol.,* 87:327 (#752), 1991.
O'Hehir et al., *Ann. Rev. Immunol.,* 9:67, 1991.
O'Hehir et al., *J. Allergy Clin. Immunol.,* 87:1120, 1991.
Rafnar et al,., *J. Biol. Chem.,* 266:1229, 1991.
Rudensky et al. (1991) Nature 353:622–7.
Silvanovich et al., *J. Biol. Chem.,* 266:1204, 1991.
Valenta et al., *Science,* 253:557, 1991.
Aruda et al., *J. Exp. Med.,* 172:1529, 1990.
King et al., *Protein Sequences and Data Analysis,* 3:263–6 1990.
King, *J. Allergy clin. Immunol.,* 85:213(#280), 1990.
Perez et al., *J. Biol. Chem.,* 265:16210, 1990.
Ansari et al., *Biochemistry,* 28:8665, 1989.
Breiteneder et al., *EMBO J.,* 8:1935, 1989.
Hynes et al. (1989) Infect Immunity 57:533–9.
Korneev et al. (1989) Bioorg. Khim. 15:127–7.
Chua et al., *J. Exp. Med.,* 167:175, 1988.
Fang et al., *Proc. Natl. Sci. USA,* 85:895–9, 1988.
Frohman et al., *Proc. Natl. Acad. Sci. USA,* 85:8998–9002, 1988.
King, *J. Allergy Clin. Immunol.,* 79: 113, 1987.
Reeck et al. (1987) Cell 50:667.
Hoffman *J. Allergy and Clin Immunol.,* 75:611, 1985.
Huynh et al. (1985) pp. 49–78 in DNA Cloning, Glover, ed., IRL Press.
King et al., *J. Allergy and Clin. Immunol.,* 75:621–8, 1985.
Lathe et al. (1985) J. Mol. Biol. 183:1–12.
King et al., *Arch. Biochem. Biophys.,* 230:1, 1984.
King et al., *J. Immunol.,* 133:2668, 1984.
King et al., *Mol. Immunol.,* 20:297, 1983.
King et al., *Biochemistry,* 17:5165, 1978.
Hoffman, D.R. J Allergy Clin. Immunol. 75(5):599–605, May, 1985.*

* cited by examiner

*Primary Examiner*—Tekchend Saidha

(57) ABSTRACT

The present invention is directed to nucleic acids encoding vespid venom phospholipases, or fragments thereof, recombinant vectors comprising such nucleic acids, and host cells containing the recombinant vectors. The invention is further directed to expression of such nucleic acids to produce recombinant vespid venom phospholipases, or recombinant fragments, derivatives or analogs thereof. Such recombinant products are useful for diagnosis of allergy and for therapeutic treatment of allergy. In specific embodiments, the present invention provides nucleic acids encoding, and complete nucleotide and amino acids sequences for, vespid venom phospholipase A1, for example, *Dolichovespula maculata* phospholipase $A_1$ and *Vespula vulgaris* phospholipase A1.

12 Claims, 7 Drawing Sheets

Figure 2A:
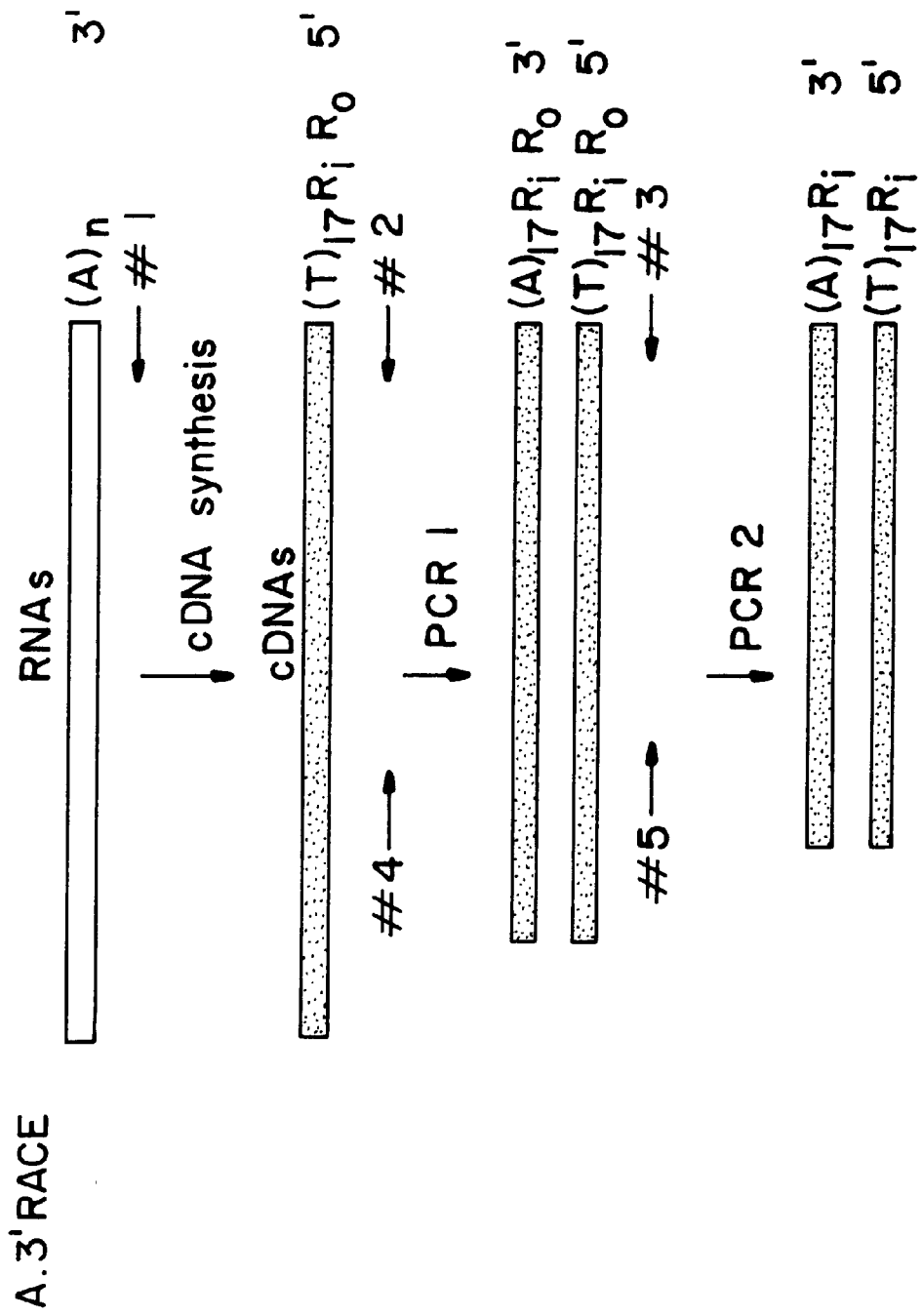

```
  R   L   I   M   F   V   G   D   P   S   S   S   N   E   L   D   R   F   S   V     3
AGATTAATAATGTTCGTAGGTGATCCGTCGTCATCAAATGAATTAGATAGATTCTCCGTA                          60

C   P   F   S   N   D   T   V   K   M   I   F   L   T   R   E   N   R   K   H    23
TGTCCCTTTAGTAATGATACAGTTAAGATGATTTTTTTAACAAGGGAAAACCGAAAACAT                         120

D   F   Y   T   L   D   T   M   N   R   H   N   E   F   K   K   S   I   I   K    43
GATTTTTATACGCTAGATACAATGAACAGGCACAATGAATTTAAGAAGTCAATCATAAAA                         180

R   P   V   V   F   I   T   H   G   F   T   S   S   A   T   E   K   N   F   V    63
CGTCCAGTTGTATTCATTACGCATGGTTTTACTTCGTCTGCAACCGAAAAAAATTTCGTT                         240

A   M   S   E   A   L   M   H   T   G   D   F   L   I   I   M   V   D   W   R    83
GCTATGTCAGAGGCTCTTATGCATACAGGTGATTTTCTTATAATTATGGTCGATTGGCGG                         300

M   A   A   C   T   D   E   Y   P   G   L   K   Y   M   F   Y   K   A   A   V   103
ATGGCTGCTTGTACTGATGAATACCCAGGTCTGAAGTATATGTTTTATAAGGCTGCCGTT                         360

G   N   T   R   L   V   G   N   F   I   A   M   I   A   K   K   L   V   E   Q   123
GGTAATACACGCTTAGTTGGAAATTTTATCGCTATGATCGCAAAGAAACTTGTAGAACAA                         420

Y   K   V   P   M   T   N   I   R   L   V   G   H   S   L   G   A   H   I   S   143
TATAAAGTGCCGATGACAAATATACGACTGGTGGGACACAGTTTGGGCGCACACATTTCA                         480

G   F   A   G   K   R   V   Q   E   L   K   L   G   K   F   S   E   I   I   G   163
GGTTTCGCAGGCAAAAGAGTTCAAGAGTTAAAATTAGGAAAATTTTCTGAAATTATTGGG                         540

L   D   P   A   G   P   S   F   K   K   N   D   C   S   E   R   I   C   E   I   183
CTTGATCCTGCTGGGCCTAGTTTCAAGAAAAATGATTGTTCCGAGAGAATCTGCGAGACA                         600

D   A   H   Y   V   Q   I   L   H   T   S   S   N   L   G   T   E   R   T   L   203
GACGCACATTATGTACAAATTTTACATACATCGAGCAATTTAGGAACAGAGAGAACTCTT                         660

G   T   V   D   F   Y   I   N   N   G   S   N   Q   P   G   C   R   Y   I   I   223
GGCACCGTCGATTTCTACATAAATAACGGAAGTAATCAACCCGGTTGCAGATATATTATT                         720

G   E   T   C   S   H   T   R   A   V   K   Y   F   T   E   C   I   R   R   E   243
GGAGAAACTTGCTCTCATACGAGAGCCGTGAAATACTTTACCGAGTGCATAAGACGCGAA                         780

C   C   L   I   G   V   P   Q   S   K   N   P   Q   P   V   S   K   C   T   R   263
TGTTGTTTAATTGGGGTCCCGCAGTCCAAGAATCCGCAGCCTGTTTCGAAGTGCACAAGA                         840

N   E   C   V   C   V   G   L   N   A   K   K   Y   P   K   R   G   S   F   Y   283
AACGAGTGCGTTTGCGTTGGATTAAACGCAAAGAAATATCCTAAAAGGGGCTCATTTTAT                         900

V   P   V   E   A   E   A   P   Y   C   N   N   N   G   K   I   I   *           300
GTACCGGTTGAAGCTGAAGCTCCATATTGCAATAACAACGGGAAAATAATTTAATTATAT                         960

AAAAAAAACATTACTATTGACACAAGTGCATTTGTTAATGATGAAATGAATAAATTACGA                        1020

TTCAAGAAAAAAAAAAAAAAAAAAAAAAAAA                                                    1050
```

FIG. 1

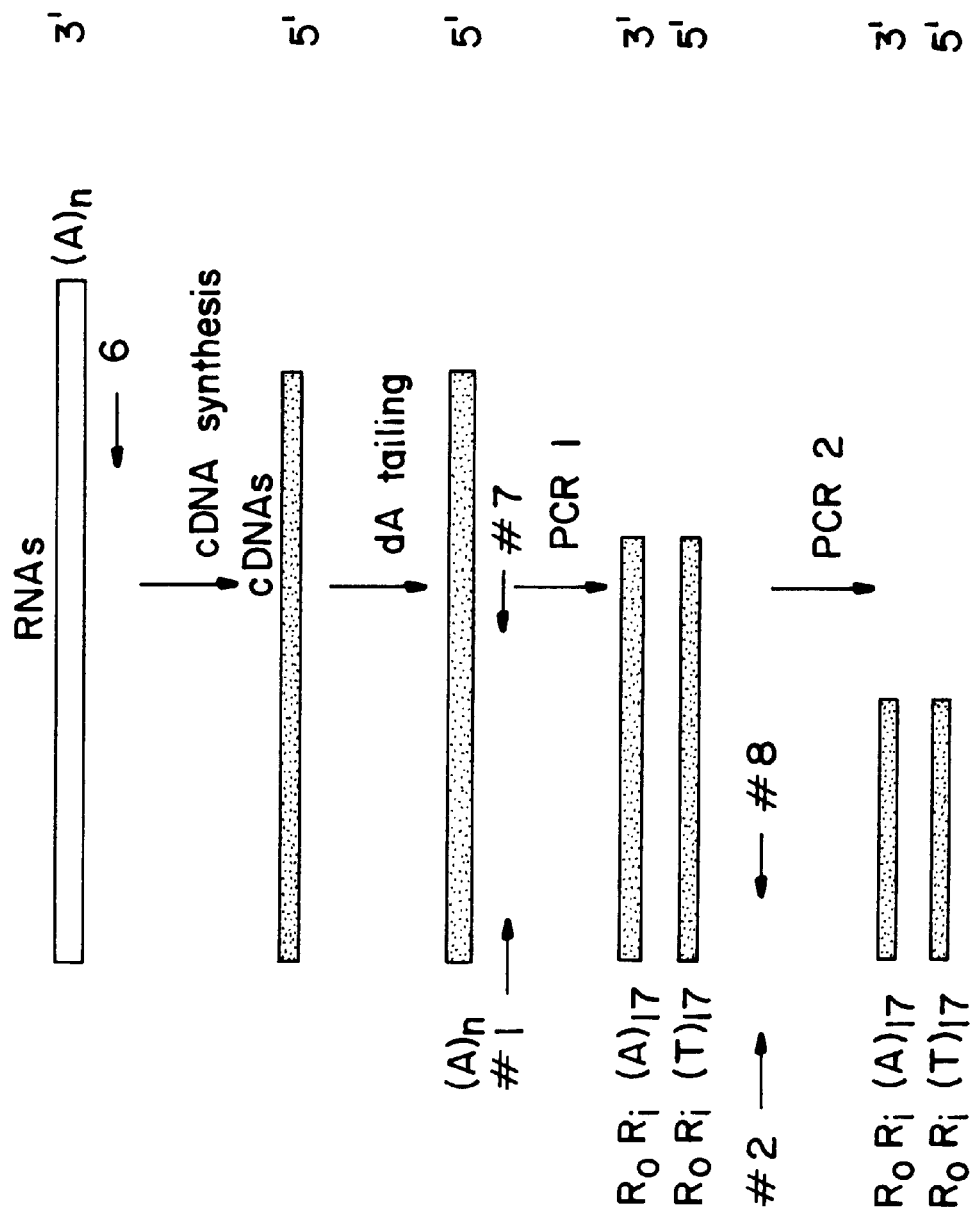

FIG. 4

```
Hu LPL    YPVSAGYTKLVGQDVARFINWMEEEFNYPLDNVHLLGYSLGAHAAGIAG    169
Mo LPL    YPVSAGYTKLVGNDVARFINWMEEEFNYPLDNVHLLGYSLGAHAAGVAG    161
Hu HL     YTIAVRNTRLVGKEVAALLRWLEESVQLSRSHVHLIGYSLGAHVSGFAG    178
Mo HL     YTQASYNTRVLGAEIAFLVQVLSTEMGYSPENVHLIPHSLGSHVAGEAG    180
Dm PLA    YKAAVGNTRLVGNFIAMIAKKLVEQYKVPMTNIRLVGHSLGAHISGFAGK   148
   P+L    Y     G T LVG    A           E     P    N  L G SLGAH  G AG
   P+H    Y   AV NTRLVG    A           E               L G SLGAH SGFAG

Hu LPL       SLTNKKVNRITGLDPAGPNFEYAEAPSRLSPDDADFVDVLHT FTRG    215
Mo LPL       SLTNKKVNRITGLDPAGPNFEYAEAPSRLSPDDADFVDVLHT FTRG    207
Hu HL        SSIGGTHKIGRITGLDAAGPLFEGSAPSNRLSPDDANFVDAIHT FTRE    226
Mo HL        RRLEGHVGRITGLDPAEPCFQGLPEEVRLDPSDAMFVDVIHTDSAPI     227
Dm PLA       RVQELKLGKFSEIIGLDPAGPSFKKNDCSERICETDAHYVQILHT       193
   P+L             K     I GLDPAGP F         R      DA V    LHT
   P+H             K     I GLD AGP F      S  R      DA V     HT

Hu LPL    SPGRSIGIQKPVGHVDIYPNGGTFQPGC                        243
Mo LPL    SPGRSIGIQKPVGHVDIYPNGGTFQPGC                        235
Hu HL     HMGLSVGIKQPIGHYDFYPNGGSFQPGC                        254
Mo HL     IPYLGFGMSQKVGHLDFFPNGGKEIPGC                        255
Dm PLA    SSNLGTERTLGTVDFYINNGSNQPGC                          219
   P+L            G        G VD Y N G  QPGC
   P+H            G        G    DFY N GS QPGC
```

FIG. 5A

```
ATTTCCGGGTAAGTTTGTGTACGTTCTACACAAACAAAATCATGAAGAAATATGA                    60
ATTTAAAGTATTTATTATTATTCGTGTATTTGTGCAAGTGTAAATTGTTGCTATGAC                  120
                                            G  P  K  C  P  F  N  S  D  T
ATGGTGATCCGTTATCTTACGAATTAGAGGACCCAAATGTCCTTTAATTCTGATA                    180
 V  S  I  I  E  T  R  E  N  R  D  L  Y  T  L  Q  T
CAGTTTCGATAATTATTGAAACGAGAGAAAACCGAAATCGTGATCTTTATACACTACAGA              240
 L  Q  N  H  P  E  F  K  K  K  T  I  T  R  P  V  V  F  I  T
CATTACAGAATCATCCTGAATTTAAGAAAAAAACTATAACACGTCCAGTTGTATTCATTA              300
 H  G  F  T  S  S  A  S  E  T  N  F  I  N  L  A  K  A  L  V
CACATGGTTTTACTTCATCTGCAAGTGAAACAAATTTCATAAATTTAGCAAAAGCTTTGG              360
 D  K  D  N  Y  M  V  I  S  I  D  W  Q  T  A  A  C  T  N  E
TAGATAAAGATAACTATATGGTTATCTCAATCGATTGGCAGACGCTGCTTGTACTAATG               420
 A  A  G  L  K  Y  L  Y  Y  P  T  A  A  R  N  T  R  L  V  G
AAGCTGCAGGTTTAAAGTATTTATATTATCCTACTGCTGCTAGAAATACACGTTTAGTTG              480
 Q  Y  I  A  T  I  T  Q  K  L  V  K  H  Y  K  I  S  M  A  N
GACAATATATCGCTACGATTACCCAGAAACTCGTAAAACACTATAAAATCTCGATGGCAA              540
 I  R  L  I  G  H  S  L  G  A  H  A  S  G  F  A  G  K  K  V
ATATACGATTAATTGGACATAGCTTAGGAGCACATGCTTCAGGTTTTGCAGGCAAAAAGG              600
 Q  E  L  K  L  G  K  Y  S  E  I  I  G  L  D  P  A  R  P  S
TTCAAGAGTTAAAATTAGGAAAATATTCTGAAATTATTGGGCTTGATCCTGCTAGGCCTT              660
```

FIG. 5B

```
        F   D   S   N   H   C   S   E   R   L   C   E   T   D   A   E   Y   V   Q   I
CGTTCGATTCAAATCATTGTTCCGAAAGACTCTGCCGAGACAGATGCAGAATAGTTCAAA      720
        I   H   T   S   N   Y   L   G   T   E   K   T   L   G   T   V   D   F   Y   M
TTATACATACATCAAACTATTTAGGAACCGAAAAACCCTTGGTACCGTCGATTTCTACA       780
        N   N   G   K   N   Q   P   G   C   G   R   F   F   S   E   V   C   S   H   S
TGAATAACGGAAAGAATCAACCTGGTGCGGTTCTAGATTTTCTCAGAAGTTTGCTCTCATT    840
        R   A   V   I   Y   M   A   E   C   I   K   H   E   C   C   L   I   G   I   P
CGAGAGCCGTGATATACATGGCTGAGTGCATAAAACACGAATGTGTTGTTAATTGGGATAC    900
        K   S   K   S   S   Q   P   I   S   S   C   T   K   Q   E   C   V   C   V   G
CGAAGTCAAAGAGTTCGCAGCCTATTTCGTCGTGCACAAAACAGGAGTGCGTTGCGTTG      960
        L   N   A   K   K   Y   T   S   R   G   S   F   Y   V   P   V   E   S   T   V
GATTAAACGCAAAGAAGTATACTAGTAGAGGCTCATTTTATGTACCGGTTGAAAGTACTG     1020
        P   F   C   N   N   K   G   K   I   I   *
TTCCTTTTTGCAATAACAAGGGGAAGATAATTTAATATATAAAAAAGTAATTTCCATTC      1080
ATCGAAATGCATTTGTTAATGGTGAATGTAATTACCATTTAACAAATAATCGTACAT        1140
GCAGAATGTCGTCCAAAATAATTGCCGAGTATATAATGGATGATCTTAGCAAATTTAAAA     1200
AATAAAAGAATTATATAAACATATACCCTATTTGATTTGCTTTTTAGTTGTAGTGAAT       1260
TGAATTTTTCGTCTGCTTAATTTGAAACTGCTTCCTTGCTTCTGAATAAATGCCCTGTAA    1320
ACATAAAAAAAAAAAAAAAA                                             1341
```

CLONING AND RECOMBINANT PRODUCTION OF VESPID VENUM PHOSPHOLIPASES, AND IMMUNOLOGICAL THERAPIES BASED THEREON

This application is a Division, of application Ser. No. 08/385,745, filed Feb. 8, 1995 now U.S. Pat. No. 5,612,209 which is a continuation of Ser. No. 08/031,400 filed Mar. 11, 1993, now abandoned.

1. FIELD OF THE INVENTION
2. BACKGROUND OF THE INVENTION
   2.1. Biochemical Aspects of Insect Venom Phospholipase
   2.2. T and B Cell Epitopes of Phospholipase
   2.3. Modulation of T and B Cell Responses
3. SUMMARY OF THE INVENTION
   3.1. Abbreviations
4. BRIEF DESCRIPTION OF THE DRAWINGS
5. DETAILED DESCRIPTION OF THE INVENTION
   5.1. Isolation of a Vespid Venom Phospholipase Gene
   5.2. Expression of a Polypeptide Comprising a Vespid Venom Phospholipase or Fragment Thereof
   5.3. Identification and Purification of the Expressed Polypeptide
   5.4. Derivatives and Analogs of Vespid Venom Phospholipase
   5.5. Assays with Recombinant Vespid Venom Phospholipase or Fragments Derivatives or Analogs Thereof
   5.6. Therapeutic and Diagnostic uses of the Vespid Venom Phospholipase or Fragments Derivatives or Analogs Thereof
6. EXAMPLE: VESPID VENOM PHOSPHOLIPASE $A_1$
   6.1. Materials and Methods
      6.1.1. Isolation and Characterization of Dol m I and its CNBr Peptides
      6.1.2. Dol m I-specific cDNA
      6.1.3. Phospholipase and Lipase Assays
   6.2. Results
      6.2.1. Partial Amino Acid Sequence of Dol m I
      6.2.2. cDNA Sequence of Dol m I
      6.2.3. Lipase Activity of Hornet Phospholipase
   6.3. Discussion
7. YELLOW JACKET PHOSPHOLIPASE $A_1$
8. DEPOSIT OF MICROORGANISMS

1. FIELD OF THE INVENTION

The present invention is directed to nucleic acids encoding a vespid venom allergen phospholipase, or fragments thereof, recombinant vectors comprising such nucleic acids, and host cells containing the recombinant vectors. The invention is further directed to expression of such nucleic acids to produce recombinant vespid venom phospholipase or recombinant fragments thereof. Such a phospholipase allergen and fragments thereof are useful for diagnosis of allergy and for therapeutic treatment of allergy.

2. BACKGROUND OF THE INVENTION

2.1. Biochemical Aspects of Insect Venom Allergens

Insect sting allergy to bees and vespids is of common occurrence. The vespids include hornets, yellowjackets and wasps (Golden, et al., 1989, Am. Med. Assoc. 262:240). Susceptible people can be sensitized on exposure to minute amounts of venom proteins as less than 10 µg of proteins is injected into the skin on a single sting by a vespid (Hoffman and Jackson, 1984, Ann. Allergy. 52:276).

There are many species of hornets (genus Dolichovespula), yellowjackets (genus Vespula) and wasp (genus Polistes) in North America (Akre, et al., 1980, "Yellowjackets of America North of Mexico," Agriculture Handbook No. 552, US Department of Agriculture). The vespids have similar venom compositions (King, et al., 1978, Biochemistry 17:5165; King, et al., 1983, Mol. Immunol. 20:297; King, et al., 1984, Arch. Biochem. Biophys. 230:1; King, et al., 1985, J. Allergy and Clin. Immunol. 75:621; King, 1987, J. Allergy Clin. Immunol. 79:113; Hoffman, 1985, J. Allergy and Clin. Immunol. 75:611). Their venom each contains three major venom allergens, allergens $A_1$ (37 kd), hyaluronidase (43 kd) and antigen 5 (23 kd) of as yet unknown biologic function.

In addition to the insect venom allergens described above, the complete amino acid sequence of several major allergens from different grass (Perez, et al., 1990, J. Biol. Chem. 265:16210; Ansari, et al., 1989, Biochemistry 26:8665; Silvanovich, et al., 1991, J. Biol. Chem. 266:1204), tree pollen (Breiteneder, 1989, EMBO J. 8:1935; Valenta, et al., 1991, Science, 253:557), weed pollen (Rafnar, et al., 1991, J. Biol. Chem. 266:1229; Griffith, et al., 1991, Int. Arch. Allergy Appl. Immunol. 96:296), mites (Chua, et al., 1988, J. Exp. Med. 167:175), cat dander (Griffith, et al., 1992, Gene. 113:263), and mold (Aruda, et al., 1990, J. Exp. Med. 172:1529; Han, et al., 1991, J. Allergy Clin. Immunol. 87:327) have been reported in the past few years. These major allergens are proteins of 10–40 kd and they have widely different biological functions. Nearly all allergens of known sequences have a varying extent of sequence similarity with other proteins in our environment.

2.2. T and B Cell Epitopes of Allergens

Antibody responses to proteins require the collaboration of T helper and B lymphocytes and antigen presenting cells (APC). The antigen receptors of B cells are the membrane-bound antibody (Ab) molecules, which recognize and bind immunogens directly. The antigen receptors of T cells (TCR) only recognize and bind complexes of antigenic peptide-MHC class II molecule. Immunogens are first processed by APC into peptides that are presented on the surface of APC in association with the MHC class II molecules (Unanue, 1992, Current opinion in Immunol 4:63). As MHC molecules are highly polymorphic in individuals, they have different specificity of binding antigenic peptides (Rothbard and Gefter, 1991, Ann. Rev. Immunol. 9:527). This is one mechanism for genetic control of immune response.

T helper cells are activated when the antigen receptor binds the peptide-MHC complex on the surface of APC. Activated T cells secrete lymphokines. In mice (Street and Mosmann, 1991, FASEB J. 5:171) and apparently in humans (Wierenga, et al., 1990, J. Immunol. 144:4651; Parronchi, et al., 1991, Proc. Natl. Acad. Sci. USA. 88:4538) the T helper cells can be divided into different types on the basis of their patterns of lymphokine production. Primarily, T helper cells divide into two groups: TH1 cells producing IL-2 and IFN-γ, and TH2 cells producing IL-4 and IL-5. These lymphokines in turn influence the antigen-activated B cells to differentiate and proliferate into plasma cells secreting Abs of different isotypes. IL-4 is one lymphokine known to influence IgE synthesis (Finkelman, et al., 1990, Ann. Rev. Immunol. 8:303).

It is believed that the entire accessible surface of a protein molecule can be recognized as epitopes by the antigen receptors of B cells, although all epitopes are not necessarily recognized with equal likelihood (Benjamin, et al., 1984, Ann. Rev. Immunol. 2:67). B cell epitopes of a protein are of two types: topographic and linear. The topographic type consists of amino acid residues which are spatially adjacent but may or may not be sequential adjacent. The linear type consists of only sequentially adjacent residues. X-ray crystallographic data of Ag-Ab complex indicate the size of their complementary binding region to have 16–17 amino acid residues (Amit, et al., 1986, Science 233:747) but peptide mapping suggests that less than about 8 residues contribute significantly to the binding process of a linear epitope (Appel, et al., 1990, J. Immunol. 144:976). Allergens, like other protein antigens, can have both types of B cell epitopes or only one. For example, vespid antigen 5s have both types and bee venom melittin appears to have only one B cell epitope of linear type (King, et al., 1984, J. Immunol. 133:2668).

T cell epitopes of proteins consist of only the linear type since they are peptides that have been processed in the lysosomes of APC by proteases of unknown specificity (Unanue, 1992, Curr. Op. Immunol. 4:63). Analysis of naturally processed antigenic peptides bound to MHC class II molecules indicates that their size range from about 13 to 17 amino acid residues, but analysis of synthetic peptide-MHC class II molecule complex for their T cell proliferate response suggests a minimal size of about 8 amino acid residues (Cf. Rudensky et al., 1991, Nature 353:622). Studies suggest that T cell epitopes are distributed throughout the entire protein molecule, and they may function as major or minor determinants depending on the MHC haplotype of the immunized host (Roy, et al., Science 244:572; Gammon, et al., 1987, Immunol. Rev. 98:53; O'Hehir et al., Ann. Rev. Immunol. 9:67).

Hypersensitivity of the immediate type is known to be caused by the presence of allergen-specific IgE. IgE is found in the circulation and bound to specific IgE-Fc receptors on mast cells and basophils. Cross-linking of cell-bound IgE by allergens leads to relese of histamine, leukotrienes and other chemical mediators that cause the allergic symptoms. IgE is one isotype of immunoglobulin. As pointed out above, lymphokines secreted by T cells influence isotype switch events in B cells.

Because of the central role of TH2 cells in determining the isotypes switch event of B cells, the T cell epitopes of several allergens have been mapped (Cf. O'Hehir et al., supra). The allergens include ragweed Amb α III, rye grass Lol p I, cat Fel d I, mouse urine Mus m I, midge Chi t I, and bee venom phospholipase $A_2$ (Dhillon, et al., 1992, J. Allergy Clin. Immunol. 90:42) and melittin (Fehlner, et al., 1991, J. Immunol. 146:799). The data do not reveal any unusual or common structural features. However, any conclusion from these data is qualified as these data are collected from humans and mice of different haplotype.

2.3. Modulation of T and B Cell Responses

Normally hosts are tolerant to the dominant B and T cell epitopes of self proteins by clonal deletion and anergy. However this tolerance can be broken under certain circumstances (Gammon, et al., 1991, Immunol. Today. 12:193; Basten, et al., 1991, Immunol. Rev. 122:5). It has been suggested that self-tolerance is broken in autoimmune diseases through encounters with foreign proteins that are similar to host proteins. Therefore the sequence similarity of allergens with autologous proteins is of interest for closer investigation.

Mature B cells are activated in response to multi-valent antigens which can cross-link cell-surface Ig receptors (DeFranco, 1987, Ann. Rev. Cell Biol. 3:143) and they are rendered anergic in response to mono-valent antigen (Basten, et al., 1991, supra). Antigen activation of T cells requires not only the integration of TCR with peptide-MHC complex but also with other co-stimulating signals on the surface of APC (Schwartz, 1990, Science 248:1349; Jenkins and Miller, 1992, FASEB J. 6:2428). Interaction of TCR with peptide-MHC complex in absence of co-stimulating signals can lead to T cell anergy.

The molecular mechanism of B or T cell anergy is not yet understood (Cf. Schwartz, 1990, supra; Jenkins and Miller, 1992, supra; Ales-Martinez, et al., 1991, Immunol. Today 12:201). In vitro studies with T cell clones revealed that occupancy of TCR by an artificial peptide-MHC complex in the absence of co-stimulating signals leads to altered intracellular signal transduction and/or repressor gene activation which can prevent lymphokine transcription.

Early studies have shown that the physical state of the immunogen and the route of immunization are important variables in determining the outcome of an immune response. In the light of our current understanding, these variables may well influence antigen presentation so as to have T and B cell activation or anergy.

Since an MHC class II molecule of any one haplotype can bind a wide range of peptides in its binding groove, it may be possible to modulate T cell response by inhibition of allergen-derived T cell epitope binding to MHC molecules with other peptides. For example, a mouse lysozyme peptide which is not immunogenic by itself in $H-2^k$ mice inhibits T cell response to hen egg white lysozyme (Adorini and Nagy, 1990, Immunol. Today. 11:21). Another example is the in vitro inhibition of T cell response to mite allergens by an influenza HA peptide (O'Hehir et al., 1991, J. Allergy Clin. Immunol. 87:1120).

Experimental autoimmune encephalomyelitis (EAE) in mice or rats is a well studied model for multiple sclerosis. Many studies have identified immunodominant T cell determinants for myelin basic protein, which is used to induce condition. Peptides that correspond to immunodominant epitopes of myelin basic protein can induce tolerance to the same peptide antigen or to the intact myelin basic protein. The same peptides that induced tolerance could also induce T cell anergy in an ongoing autoimmune response (Gaur et al., 1992, Science 259:1491–1494).

Immune response to an immunogen/allergen depends on the genetic make-up of the host, the route and mode of immunization and the immunogen/allergen. The extent to which a vespid venom allergen determines the outcome of IgE response is not known. How many B and T cell epitopes does each vespid venom allergen have? Are there immunodominant B or T cell epitopes of a vespid venom allergen recognized by different or all susceptible individuals? Are there T cell epitopes which favor IgE class switch events in B cells? Does antigenic cross reactivity of vespid venom allergens with host proteins play a role as to why some proteins are more allergenic than others are? Can tolerance to a multi-valent vespid venom allergen be induced by treatment with a single or a combination of B or T cell epitopes?

Thus, there is a need in the art to delineate the B and helper T cell epitopes of major vespid venom allergens, in particular, the B cell epitopes of the linear type. There is a particular need to delineate the B and helper T cell epitopes of the vespids hornet (e.g., *Dolichovespula arenaria*), yellowjacket (e.g., *Vespula vulgaris*) and wasp (e.g., *Polistes annularis*). In particular, one of the major vespid venom allergens, phospholipase $A_1$, is an appropriate target for determining the important B and T cell epitopes. In order to fully address the basis for allergic response to vespid allergens, and to develop allergen-based immunotherapies, the cDNA and protein sequences of several homologous allergens need to be investigated. Moreover, vectors suitable for high level expression in bacteria and eukaryotic cells of vespid allergens or their fragments should be developed. The recombinant vespid allergens and their fragments may then be used to map their B and T cell epitopes in the murine and, more importantly, human systems by antibody binding and T cell proliferation tests, respectively.

There is a further need to determine whether there is cross reaction of the T and B cell epitopes of vespid allergens with other environmental and/or autologous proteins. Thus there is a need to determine whether vespid allergens share partial identity with other environmental proteins, especially with autologous proteins, and more importantly, to obtain the sequences of the regions of the partial identity, in particular the specific amino acid sequences of such regions of partial identity. There is a further need to determine the level of cross reactivity of vespid allergens with other proteins at the B cell and T cell level, the relevance of this cross reactivity, and whether such cross reactivity is pathological, i.e., involved in or responsible for allergy, or beneficial, i.e., inhibitory of allergy.

There is also a need in the art to use peptides having T or B cell epitopes of vespid venom allergens to study induction of tolerance in mice and induction of tolerance in humans.

There is a further need to test whether a modified peptide inhibits allergen T cell epitope binding to MHC class II molecule, or induces T cell anergy, or both.

Thus, there is a need in the art for the sequence information about vespid venom allergens, and a plentiful source of such allergens for immunological investigations and for immunological therapy of the allergy.

Citation of references hereinabove shall not be construed as an admission that such is prior art to the present invention.

3. SUMMARY OF THE INVENTION

The present invention provides nucleic acids encoding vespid venom phospholipases, and immunomodulatory fragments, derivatives or analogs thereof. In particular, the invention is directed to nucleic acids encoding vespid venom phospholipases $A_1$, for example, *Dolichovespula maculata* phospholipase $A_1$, and *Vespula vulgaris* phospholipase $A_1$. In specific embodiments, a nucleic acid of the invention encodes an immunomodulatory portion of a T cell epitope of a vespid venom phospholipase. In another specific embodiment, a nucleic acid of the invention encodes an antigenic portion of a B cell epitope of a vespid venom phospholipase. Expression of the nucleic acids of the invention provides a plentiful source of the vespid phospholipase for diagnosis and therapy.

It is a particular advantage of the present invention that the nucleic acid sequences encoding a number of vespid venom phospholipases are provided. Such nucleic acid sequences allow deduction of the amino acid sequence of the vespid venom phospholipases. Knowledge of the amino acid sequence allows for the determination of relevant T cell and B cell epitopes of the phospholipase. More importantly, the immunodominant T cell and B cell epitopes can be determined for each phospholipase-sensitive individual or group of-individuals, i.e., who share a susceptible MHC haplotype, or for whom the T cell epitope favors class switch events to IgE class antibodies. Once such T cell and B cell epitopes are determined, it is possible to devise immunological therapies for vespid venom phospholipase-specific allergic conditions.

Thus, the instant invention further provides polypeptides encoded by the nucleic acids of the invention. In particular, the invention provides polypeptides having an immunomodulatory portion of a T cell epitope of the vespid venom phospholipase. In another embodiment, the invention provides polypeptides having an antigenic portion of a B cell epitope of the vespid venom phospholipase. More particularly, the invention provides such polypeptides of a vespid venom phospholipase $A_1$, for example, *Dolichovespula maculata* phospholipase $A_1$ and *Vespula vulgaris* phospholipase A1.

The present invention further provides expression vectors comprising the nucleic acids of the invention operationally associated with a promoter. The present invention also provides methods for producing the vespid venom phospholipases encoded by the nucleic acids of the invention. In particular, the invention provides for culturing a cell transformed with an expression vector of the invention so that the vespid venom phospholipase is expressed by the cell, and recovering the vespid venom phospholipase so expressed from the culture. More particularly, the invention provides for expression of expression vectors comprising nucleic acids encoding a vespid venom phospholipase $A_1$, for example, *Dolichovespula maculata* phospholipase $A_1$ and *Vespula vulgaris* phospholipase A1, or fragments, derivatives or analogs thereof.

In yet another embodiment, the present invention provides a pharmaceutical composition effective for the treatment of a vespid venom allergen-specific allergic condition comprising a polypeptide of the invention that has an immunomodulatory portion of a T cell epitope of a vespid venom phospholipase or an antigenic portion of a B cell epitope of a vespid venom phospholipase. More particularly, the invention provides pharmaceutical compositions comprising such polypeptides of a vespid venom phospholipase $A_1$, for example, *Dolichovespula maculata* phospholipase $A_1$ and *Vespula vulgaris* phospholipase $A_1$.

In yet still another embodiment, the present invention provides a method for treating a vespid venom allergen-specific condition comprising administering a therapeutically effective dose of a pharmaceutical composition of the invention.

Thus, an advantage of the invention is that it provides for production of many vespid venom phospholipases, which can be used therapeutically for the treatment of vespid venom phospholipase-specific allergic conditions. Most importantly, the therapeutic treatment can be highly specific and individualized, since the invention allows production of a vespid venom phospholipase polypeptide that has immunomodulatory activity in any individual or group of individuals.

It is another particular advantage of the present invention to have the nucleic acid sequences and deduced amino acid sequences of a large number of various vespid venom phospholipases from different species to allow comparison of the homology of analogous phospholipases between species. This information provides a basis for evaluating cross-reactivity of the phospholipases, which can be important for allergic reactions and for therapeutic treatments.

It is a further advantage of the present invention that the degree of similarity of many vespid venom phospholipases to environmental proteins and/or autologous proteins can be evaluated. It is believed that similarity of the vespid venom phospholipases to such environmental proteins, and particularly to autologous proteins, has important implications for the allergic response.

3.1. ABBREVIATIONS

| Dol m | Dolichovespula maculata | white face hornet |
|---|---|---|
| Dol a | D. arenaria | yellow hornet |
| Pol a | Polistes annularis | wasp |
| Pol e | P. exclamans | wasp |
| Ves m | Vespula maculifrons | yellowjacket |
| Ves v | V. vulgaris | yellowjacket |
| PCR | polymerase chain reaction | |
| RACE | rapid amplification of cDNA ends | |
| TCR | T cell receptor for antigen | |

4. BRIEF DESCRIPTION OF THE DRAWINGS

FIG. 1. cDNA and amino acid sequences of hornet phospholipase $A_1$ (Dol n I). Nucleotide and amino acid positions are numbered on the right. Numbering of amino acid residues begins and ends at the N- and C-termini of phenylalanine and isoleucine, respectively, corresponding to nucleotide positions of 52–54 and 949–951; these amino acid residues and nucleotides are shown in bold characters. The underlined amino acid residues were also established by Edman degradation of CNBr peptides.

FIG. 2. Schematic diagram for rapid amplification of the 3' (A) and 5' (B) cDNA ends (RACE) of Dol m I. Open and solid bars represent RNA and DNA respectively. The oligonucleotide primers are numbered, and their sequences are given in Table 1.

Figure 3:
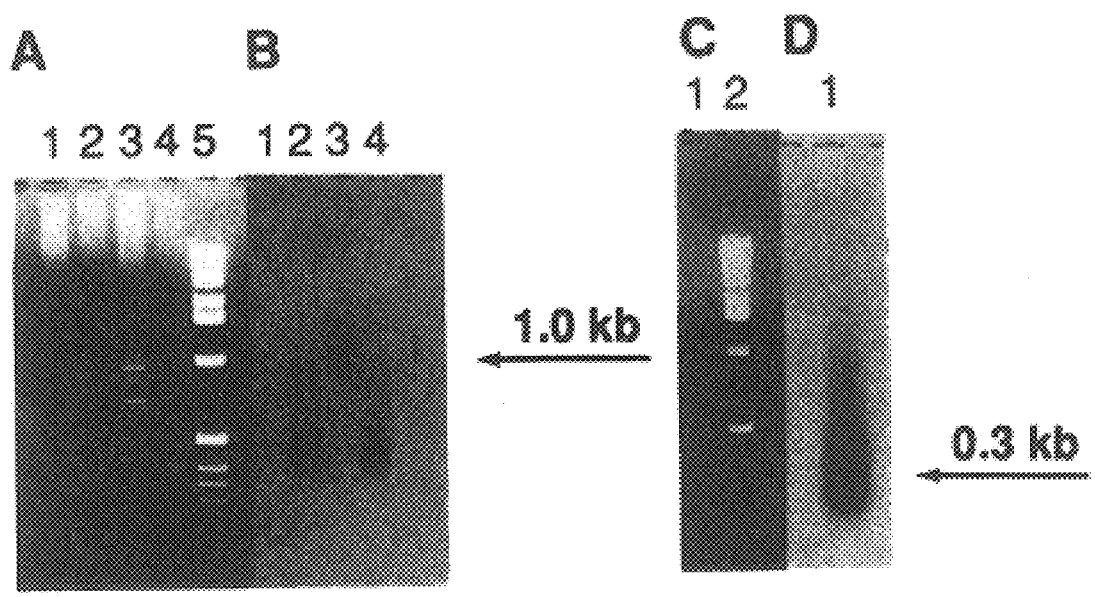

FIG. 3. 3' and 5' RACE of white-faced hornet phospholipase-specific cDNA. In panels A and B are shown respectively the agarose gel electrophoresis and Southern blot analysis products for 3' RACE. In lanes 1 and 3 are shown the products from first and second rounds of PCR obtained with AmpliTaq DNA polymerase, in lanes 2 and 4 are shown similar products obtained with Vent polymerase; and in lane 5 is shown a 1 kb DNA Ladder (BRL). In panels C and D are shown similar results (as in panels A and B) for 5' RACE products (lane 1) obtained with AmpliTaq DNA polymerase; and in lane 2 (panel C) is shown the 1 kb DNA Ladder. The arrows in panels B and D indicate the desired products. The hybridization probes are given in Table 1.

FIG. 4. Sequence similarity of Dol m I and mammalian lipases. Amino acid positions are numbered on the right. Abbreviations used: Hu, human; Mo, mouse; LPL, lipoprotein lipase; HL, hepatic lipase; Dm, white face hornet; and PLA, phospholipase. P+L and P+H indicate residues of hornet phospholipase which are identical to human lipoprotein or hepatic lipases respectively.

FIGS. 5A and 5B. cDNA and deduced amino acid sequence of yellowjacket phospholipase $A_1$. Nucleotide positions are numbered on the right. Nucleotides 1–152 correspond to the 5'-untranslated region and leader sequence. Nucleotides 153–1052 encode the mature protein. Nucleotides 1053–1341 correspond to the 3'-untranslated region. Underlined portions of the amino acid sequence were also established by Edman degradation of CNBr peptides. Note that the N-terminal sequence of natural venom was found to be FPKCP . . . , but the N-terminus translated from the cDNA is G PKCP. . . .

5. DETAILED DESCRIPTION OF THE INVENTION

The present invention is directed to recombinant nucleic acids encoding vespid venom phospholipases, and immunomodulatory fragments, derivatives or analogs thereof, and polypeptides encoded by such nucleic acids useful in the diagnosis and therapy of vespid venom-specific allergy. In particular, the present invention is directed to a recombinant nucleic acid encoding an immunomodulatory fragment of a vespid phospholipase $A_1$, in particular Dolichovespula maculata (white-face hornet) phospholipase $A_1$ (Dol m I) and Vespula vulgaris (yellowjacket) phospholipase $A_1$ (Ves v I).

The invention is further directed to expression vectors comprising such nucleic acids, and to methods for producing vespid venom phospholipase polypeptides of the invention by expressing such expression vectors and recovering the expressed vespid venom phospholipase polypeptides.

The invention also provides pharmaceutical compositions effective for the treatment of a vespid venom allergen-specific allergic condition comprising a polypeptide of the invention, and methods for treating such allergic conditions comprising administering a therapeutically effective dose of the pharmaceutical compositions of the invention.

The polypeptides of the invention can also be useful for diagnosis of vespid venom-specific allergic conditions.

As used herein, the term "vespid venom allergen" refers to a protein found in the venom of a vespid, to which susceptible people are sensitized on exposure to the sting of the insect. While most antigens are characterized by being reactive with specific IgG class antibodies, an allergen is characterized by being reactive with IgE type antibodies. The IgE type antibodies are responsible for mediating the symptoms of an allergic condition, i.e., immediate-type hypersensitivity.

As herein, the term "vespid" is used according to the practice of those in the field of allergy, and refers to insects belonging to the worldwide family of Vespidae, i.e., social wasps including hornets, yellowjackets, and paper wasps. In particular, vespids include the subfamilies Vespinae and Polistinae. More particularly, the vespids include the genera Vespa Linnaeus, Vespula Thomson, Dolichovespula Rohwer, and Polistes Latreille. Species in the genus Vespula include but are not limited to V. germanica (Fab.), V. squamosa (Drury), V. maculifrons (Buysson), V. flavopilosa (Jacobson), V. vulgaris (L.), and V. pensylvanica (Saussure). Species in the genus Polistes include but are not limited to P. annularis (Linnaeus), P. exclamans (Viereck), P. metricus (Say), P. fuscatus (Fabricius), and P. apachus (Saussure). Species in the genus 35 Dolichovespula include but are not limited to D. maculata (L.) and D. arenaria (Fab.). Species in the genus Vespa include but are not limited to V. crabro (L.) and V. orientalis (Linnaeus).

As used herein, the term "phospholipase" refers 5 to the class of enzymes that act on phopholipid substrates, e.g., to hydrolyze fatty acids. In a specific embodiment a phospholipase catalyzes rapid hydrolysis of the acyl group at polition 1 of synthetic phosphatidylcholines, and a slow hydrolysis of the acyl group at position 2. Thus, the vespid phospholipases of the invention can have both $A_1$ and B types of phospholipase activities. The phospholipases of the invention can have low level lipase activity as well.

As used herein, the term "immunomodulatory" refers to an ability to increase or decrease an antigen-specific immune response, either at the B cell or T cell level. Immunomodulatory activity can be detected in vitro, e.g., in T cell proliferation assays, or in vivo, e.g., by measurement of antibody production, lymphokine production or T cell responsiveness. In particular, in addition to affecting T cell responses, the immunomodulatory polypeptides of the invention may bind to immunoglobulin (i.e., antibody) molecules on the surface of B cells, and affect B cell responses as well.

The present invention is based, in part, on the cloning and sequence determination of various vespid venom phospholipase $A_1$s. The cloning and sequence determination of these vespid venom phospholipases is of great importance, since vespid venom allergic conditions are common, and in some sensitive individuals an allergic reaction can proceed to anaphylaxis, which is potentially fatal. It is therefore of great importance that the nucleotide and amino acid sequence information for the vespid venom allergens is known so that accurate diagnostic information about the nature of the allergic condition, especially specific allergen sensitivities, can be determined and effective therapeutic treatments of the underlying allergic condition can be effected.

For the sake of clarity, the present invention is described in detail in sections relating to isolation of genes encoding vespid venom phospholipases, expression of a polypeptide comprising an immunomodulatory fragment of a vespid venom phospholipase, or derivatives and analogs of the vespid venom phospholipase, assays with the recombinant vespid venom phospholipase, or fragments, derivatives or analogs thereof, and finally therapeutic and diagnostic uses of the vespid venom phospholipase, or fragments, derivatives or analogs thereof.

5.1. Isolation of a Vespid Venom Phospholipase Gene

The invention relates to isolated nucleic acids encoding vespid venom phospholipases. The invention further relates to a cell line stably containing a recombinant nucleic acid encoding a vespid venom phospholipase, and capable of expressing such nucleic acid to produce the protein or an immunomodulatory fragment of a vespid venom phospholipase.

Derivatives of a vespid venom phospholipase, such as fragments and fusion proteins (see Section 5.4), are additionally provided, as well as nucleic acids encoding the same.

In a preferred aspect, the present invention provides the complete nucleic acid sequence of a vespid venom phospholipase. In particular, the present invention provides the nucleic acid sequence of a vespid phospholipase $A_1$, in particular *Dolichovespula maculata* (white-face hornet) phospholipase $A_1$ (Dol m I) and *Vespula vulgaris* (yellowjacket) phospholipase $A_1$ (Ves v I).

In a more preferred aspect of the invention, the complete nucleic acid encoding *Dolichovespula maculata* (white-face hornet) phospholipase $A_1$ (Dol m I) can be obtained from the microorganism deposited with the ATCC as described in Section 8, infra.

In a specific embodiment, to obtain a nucleic acid encoding a vespid venom phospholipase, polymerase chain reaction (PCR) is combined with the rapid amplification of cDNA ends (RACE) technique described by Frohman et al. (1988, Proc. Nat. Acad. Sci. USA 85:8998–9002; see also Frohman, 1990, Amplifications: A Forum for PCR Users 5:11) to amplify a fragment encoding a sequence comprising the a vespid venom phospholipase prior to selection. Oligonucleotide primers representing a vespid venom phospholipase of the invention can be used as primers in PCR. Preferably, such primers are prepared synthetically. Sequences for such oligonucleotide primers can be deduced from amino acid sequence information. More preferably, the primers are based on the nucleic acid sequences for the vespid venom phospholipases disclosed herein. The oligonucleotides may be utilized as primers to amplify by PCR sequences from a source (RNA or DNA), preferably a cDNA library, of potential interest. For example, PCR can be used to amplify a vespid venom phospholipase coding sequence from a vespid acid gland cDNA library. PCR can be carried out, e.g., by use of a Perkin-Elmer Cetus thermal cycler and Taq polymerase (Gene Amp™).

The present invention further provides for isolating a homolog of a vespid venom phospholipase from any species of vespid. One can choose to synthesize several different degenerate primers for use, e.g., in PCR reactions. It is also possible to vary the stringency of hybridization conditions used in priming PCR reactions, to allow for greater or lesser degrees of nucleotide sequence similarity between a homolog of a vespid venom phospholipase and a specific vespid venom phospholipase disclosed herein. After successful amplification of a segment of a homolog of a vespid venom phospholipase, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding vespid venom phospholipases, in particular, phospholipases $A_1$, may be identified and expressed.

In another embodiment, genes encoding a vespid venom phospholipase can be isolated from a suitable library by screening with a probe. Useful probes for isolating a vespid venom phospholipase gene can be generated from the sequence information provided herein.

An expression library can be constructed by methods known in the art. Preferably, a cDNA library is prepared from cells or tissues that express a vespid 20 venom phospholipase, i.e., cells from the venom sac acid gland. For example, mRNA is isolated, cDNA is made and ligated into an expression vector (e.g., a bacteriophage derivative) such that it is capable of being expressed by the host cell into which it is then introduced. Various hybridization screening assays using probes derived from the nucleic acid sequences disclosed in the instant application can then be used to select for the expressed vespid phospholipase. It has been found, however, that anti-vespid venom phospholipase antibodies may not be useful for selection from a bacterial expression library, e.g., a λgt library. In another embodiment, phospholipase $A_1$ or B, or lipase activity of the expressed vespid venom phospholipase can be used for selection.

The above-methods are not meant to limit the following general description of methods by which clones of a vespid venom phospholipase may be obtained.

Any vespid acid gland potentially can serve as the nucleic acid source for the molecular cloning of a vespid venom phospholipase. The nucleic acid sequences encoding a vespid venom phospholipase can be isolated from any vespid, such as hornet, yellowjacket, or paper wasp sources. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired a vespid venom phospholipase gene may be accomplished in a number of ways. For example, a nucleic acid probe based on the nucleotide sequences disclosed herein can be synthesized and labeled, and the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene, e.g., phospholipase or lipase activity of a vespid phospholipase encoded by the gene.

Alternatively, the presence of the gene may be detected by assays based on the physical, chemical, or immunological properties of its expressed product. Fo:r example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for a vespid venom phospholipase. In another embodiment, an antibody can be used to select for a recombinant vespid venom phospholipase of the invention.

Alternatives to isolating the vespid venom phospholipase genomic DNA or cDNA include, but are not limited to, chemically synthesizing the gene sequence itself from the sequence provided herein or making cDNA to the imRNA which encodes the a vespid venom phospholipase protein. For example, RNA for cDNA cloning of the a vespid venom phospholipase gene can be isolated from cells which express a vespid venom phospholipase, such as vespid acid gland cells. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 derivatives or pUC plasmid derivatives, e.g., PGEX vectors, pmal-c, pFLAG, etc. The insertion into a cloning vector can, for example, be accomplished by ligating the DNA fragment into a cloning vector which has complementary cohesive termini. In a preferred aspect of the invention, the PCR amplified nucleic acids of the invention contain 3'-overhanging A-nucleotides, and can be used directly for cloning into a PCR vector with compatible T-nucleotide overhangs (Invitrogen Corp., San Diego, Calif.). However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and a vespid venom phospholipase gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated vespid venom phospholipase gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.2. Expression of a Polypeptide Comprising a Vespid Venim Phospholipase or Fragment Thereof The nucleotide sequence coding for a vespid venom phospholipase, or an immunomodulatory fragment, derivative or analog thereof (see Section 5.4), can be inserted into an appropriate expression vector, i.e., a vector which contains the necessary elements for the transcription and translation of the inserted protein-coding sequence. Such elements are termed herein a "promoter." Thus, the nucleic acid encoding the vespid venom phospholipase is operationally associated with the promoter. An expression vector also preferably includes a replication origin. The necessary transcriptional and translational signals can also be supplied by the native gene encoding a vespid venom phospholipase and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In an alternative embodiment, a recombinant vespid venom phospholipase of the invention, or an immunomodulatory fragment, derivative or analog thereof, is expressed chromosomally, after integration of the vespid venom phospholipase coding sequence by recombination. In this regard, any of a number of amplification systems may be used to achieve high levels of stable gene expression. (See Sambrook et al., 1989, supra, at Section 16.28)

The cell into which the recombinant vector comprising the nucleic acid encoding the vespid venom phospholipase is cultured in an appropriate cell culture medium under conditions that provide for expression of the vespid venom phospholipase by the cell. The expressed vespid venom phospholipase can then be recovered from the culture according to methods well known in the art. Such methods are described in detail in Section 5.3, infra.

In a another embodiment, a vespid venom phospholipase-fusion protein can be expressed. A vespid venom phospholipase-fusion protein comprises at least a functionally active portion of a non-vespid venom phospholipase protein joined via a peptide bond to at least an immunomodulatory portion of a vespid venom phospholipase. The non-vespid venom phospholipase sequences can be amino- or carboxyl-terminal to the vespid venom phospholipase sequences. A recombinant DNA molecule encoding such a fusion protein comprises a sequence encoding at least a functionally active portion of a non-vespid venom phospholipase joined in-frame to the coding sequence for a vespid venom phospholipase, and preferably encodes a cleavage site for a specific protease, e.g., Factor Xa, preferably at the juncture of the two proteins.

In another specific embodiment, a fragment of the vespid venom phospholipase is expressed as a free (non-fusion) protein.

In a specific embodiment, infra, the vespid venom phospholipase, and immunomodulatory fragments thereof, are expressed with an additional sequence comprising about six histidine residues, e.g., using the pQE12 vector. The presence of the histidine makes possible the selective isolation of recombinant proteins on a Ni-chelation column.

In another embodiment, a periplasmic form of the fusion protein (containing a signal sequence) can be produced for export of the protein to the *Escherichia coli* periplasm. Export to the periplasm can promote proper folding of the expressed protein.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a vespid venom phospholipase, or an immunomodulatory fragment thereof, may be regulated by a second nucleic acid sequence so that the vespid venom phospholipase protein or peptide is expressed in a host transformed with the recombinant DNA molecule. For example, expression of a vespid venom phospholipase protein may be controlled by any promoter/enhancer element known in the art, but these regulatory elements must be functional in the host selected for expression. Promoters which may be used to control a vespid venom phospholipase gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a vespid venom phospholipase can be identifiecl by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted vespid venom phospholipase gene. In the third approach, the recombinant vector/host system can be identified and selected based upon the presence or absence of certain "marker" gene functions (e.g., β-galactosidase activity, hymidine kinase activity, resistance to antibiotics, ransformation phenotype, occlusion body formation in aculovirus, etc.) caused by the insertion of foreign genes in the vector. In a specific example, the fusion protein comprises the "marker" gene product and a vespid venom phospholipase. In another example, if the nucleic acid encoding a vespid venom phospholipase is inserted within the marker gene sequence of the vector, recombinants containing the vespid venom phospholipase insert can be identified by the absence of the marker gene function. In the fourth approach, recombinant expression vectors can be identified by assaying for the activity of the gene product expressed by the recombinant. Such assays can be based, for example, on the physical or functional properties of the a vespid venom phospholipase gene product in in vitro assay systems, e.g., phospholipase or lipase activity, or binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered a vespid venom phospholipase may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the phospholipase protein expressed in bacteria may not be properly folded. Expression in yeast can produce a glycosylated product. Expression in insect cells can be used to increase the likelihood of "native" glycosylation and folding of a heterologous vespid venom phospholipase. Furthermore, different vector/host expression systems may affect processing reactions, such as proteolytic cleavages, to a different extent. It is interesting to note that it has been observed that glycosylation and proper refolding are not essential for immunomodulatory activity of a vespid venom allergen since bacterial-produced allergen is active in a T cell proliferation assay.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Both cDNA and genomic sequences can be cloned and expressed.

It is further contemplated that the vespid venom phospholipases of the present invention, or fragments, derivatives or analogs thereof, can be prepared synthetically, e.g., be solid phase peptide synthesis.

5.3. Identification and Purification of the Expressed Polypeptide

Once the recombinant vespid venom phospholipase protein is identified, it may be isolated and purified by standard methods including chromatography (e.g., ion exchange, affinity, and sizing column chromatography), centrifugation, differential solubility, or by any other standard technique for the purification of proteins.

In a specific embodiment, a vespid venom phospholipase and fragments thereof can be engineered to include about six histidyl residues, which makes possible the selective isolation of the recombinant protein on a Ni-chelation column. In a preferred aspect, the proteins are further purified by reverse phase chromatography.

In another embodiment, in which recombinant vespid venom phospholipase is expressed as a fusion protein, the non-vespid venom phospholipase portion of the fusion protein can be targeted for affinity purification. For example, antibody specific for the non-vespid venom phospholipase portion of the fusion protein can be immobilized on a solid support, e.g., cyanogen bromide-activated Sepharose, and used to purify the fusion protein. In another embodiment, a binding partner of the non-vespid venom phospholipase portion of the fusion protein, such as a receptor or ligand, can be immobilized and used to affinity purify the fusion protein.

In one embodiment, a vespid venom phospholipase-fusion protein, preferably purified, is used without further modification, i.e., without cleaving or otherwise removing the non-vespid venom phospholipase-portion of the fusion protein. In a preferred embodiment, the vespid venom phospholipase-fusion protein can be used therapeutically, e.g., to modulate an immune response.

In a further embodiment, the purified fusion protein is treated to cleave the non-vespid venom phospholipase protein or portion thereof from the vespid venom phospholipase. For example, where the fusion protein has been prepared to include a protease sensitive cleavage site, the fusion protein can be treated with the protease to cleave the protease specific site and release vespid venom phospholipase. In a specific embodiment, the fusion protein is cleaved by treatment with Factor Xa.

In a further embodiment, the vespid venom phospholipase protein can be refolded.

In a specific embodiment of the present invention, such recombinant vespid venom phospholipase include but are not limited to those containing, as a primary amino acid sequence, all or part of the amino acid sequence substantially as depicted in FIG. 1 (SEQ ID. NO: 17) or 5 (SEQ ID. NO: 27), as well as fragments and other derivatives, and analogs thereof.

5.4. Derivatives and Analogs of Vespid Venom Phospholipase

The invention further relates to derivatives and analogs of vespid venom phospholipases. The production and use of derivatives and analogs related to vespid venom phospholipases are within the scope of the present invention. The derivative or analog is immunomodulatory, i.e., capable of modulating an antigen-specific immune response. In another embodiment, the derivative or analog can bind to a vespid venom phospholipase-specific immunoglobulin, including IgG and IgE. Derivatives or analogs of vespid venom phospholipase can be tested for the desired immunomodulatory activity by procedures known in the art, including but not limited to the assays described in Section 5.5.

In particular, vespid venom phospholipase derivatives can be made by altering the nucleic acid sequences of the invention by substitutions, additions or deletions that provide for functionally equivalent molecules. Due to the degeneracy of nucleotide coding sequences, other DNA sequences which encode substantially the same amino acid sequence as a nucleic acid encoding a vespid venom phospholipase may be used in the practice of the present invention. These include but are not limited to nucleotide sequences comprising all or portions of a gene encoding the vespid venom phospholipase that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a vespid venom phospholipase, including altered sequences in which functionally equivalent amino acid residues are substituted for residues within the sequence resulting in a conservative amino acid substitution. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of vespid venom phospholipase include but are not limited to those which are substantially homologous to a vespid venom phospholipase or fragments thereof, or whose encoding nucleic acid is capable of hybridizing to a nucleic acid encoding a vespid venom phospholipase. Hybridization can occur under moderately stringent to highly stringent conditions, depending on the degree of sequence similarity, as is well known in the art.

The derivatives and analogs of the invention can be produced by various methods known in the art. The manipulations which result in their production can occur at the gene or protein level. For example, the nucleic acid sequence of the cloned vespid venom phospholipase can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a vespid venom phospholipase, care should be taken to ensure that the modified gene remains within the same translational reading frame as vespid venom phospholipase, uninterrupted by translational stop signals.

Additionally, the gene encoding a vespid venom phospholipase can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Manipulations of the recombinant vespid venom phospholipase may also be made at the protein level. Included within the scope of the invention are recombinant vespid venom phospholipase fragments or other derivatives or analogs which are differentially modified during or after translation, e.g., by glycosylation, acetylation, phosphorylation, amidation, reduction and carboxymethylation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In a particular embodiment, the vespid venom phospholipase or imunomodulatory fragment thereof is expressed in an insect cell expression system, e.g., using a baculovirus expression vector. As pointed out above, this should yield "native" glycosylation and structure, particularly secondary and tertiary structure., of the expressed polypeptide. Native glycosylation and structure of the expressed polypeptide may be very important for diagnostic uses, since the phospholipase specific antibodies detected in diagnostic assays will be specific for the native phospholipase, i.e., as introduced by a sting from a vespid.

5.5. Assays with Recombinant Vespid Venom Phospholipase or Fragments Derivatives or Analogs Thereof Numerous assays are known in immunology for evaluating the immunomodulatory activity of an antigen. For example, the proteins produced by expression of the nucleic acids of the invention can be used in diagnostic assays for allergic diseases, which are described in detail in Section 5.6, infra. In general, such proteins can be tested for the ability to bind to antibodies specific for the phospholipase. Preferably, such antibodies that are detected in the diagnostic assay are of the IgE class. However, it is important to note that natural allergen-specific antibodies have been found to bind weakly to denatured vespid venom allergens. Thus, vespid venom phospholipases produced in eukaryotic expression systems, and particularly insect cell expression systems, may have the correct structure for antibody binding. Vespid venom phospholipases expressed in bacterial expression systems may not, and would thus require refolding prior to use in a diagnostic assay for antibody binding.

In another embodiment, the proteins of the invention can be tested in a proliferation assay for T cell responses. For such T cell response assays, the expression system used to produce the phospholipase does not appear to affect the immunomodulatory activity of the protein. Generally, lymphocytes from a sensitized host are obtained. The host can be a mouse that has been immunized with a vespid venom phospholipase, including a vespid venom phospholipase that has been produced recombinantly according to the present invention. In a preferred embodiment, peripheral blood leukocytes are obtained from a human who is sensitive to vespid venom. Using techniques that are well known in the art, T lymphocyte response to the protein can be measured in vitro. In a specific embodiment, infra, T cell responses are detected by measuring incorporation of $^3$H-thymidine, which increases with DNA synthesis associated with proliferation. Cell proliferation can also be detected using an MTT assay (Mossman, 1983, J. Immunol. Methods 65:55–63; Niks and Otto, 1990, J. Immunol. Methods 130:140–151). Any method for detecting T cell proliferation known in the art can be used with the vespid phospholipase produced according to the present invention.

Similarly, lymphokine production assays can be practiced according to the present invention. In one embodiment, lymphokine production can be assayed using immunological or co-stimulation assays (see, e.g., Fehlner et al., 1991, J. Immunol. 146:799) or using the ELISPOT technique (Czerkinsky, et al., 1988, J. Immunol.

Methods 110:29). Alternatively, mRNA for lymphokines can be detected, e.g., by amplification (see Brenner, et al., 1989, Biotechniques 7:1096) or in situ hybridization (see, e.g., Kasaian and Biron, 1989, J. Immunol. 142:1287). Of particular interest are those individuals whose T cells produce lymphokines associated with IgE isotype switch events, e.g., IL-4. Also of interest are the polypeptide fragments of the vespid venom phospholipase that contain epitopes recognized by T cells involved in IgE switch events.

Thus, in a preferred aspect, the proteins produced according to the present invention can be used in in vitro assays with peripheral blood lymphocytes or, more preferably, cell lines derived from peripheral blood lymphocytes, obtained from vespid venom phospholipase sensitive individuals to detect secretion of lymphokines ordinarily associated with allergic responses, e.g., IL-4. Such assays may indicate which venom component or components are responsible for the allergic condition. More importantly, the fragments of the vespid venom phospholipase can be tested. In this way, specific epitopes responsible for T cell responses associated with allergic response can be identified. The sequences of such epitopes can be compared to other vespid phospholipase and to environmental or autologous proteins to determine if there are sequence similarities that suggest possible cross-reactivity. The peptides can be tested for the ability to induce T cell anergy, e.g., by mega-dose administration, modification to produce an epitope antagonist, administration in the absence of the appropriate costimulatory signals, and other methods thought to result in T cell anergy. Moreover, peptides containing such epitopes are ideal candidates for therapeutics.

In a further embodiment, the polypeptides of the invention can be used directly in assays to detect the extent of cross-reactivity with other environmental proteins and/or homologous proteins, with which they share sequence similarity. In particular, the fragments of the vespid venom phospholipase that have sequence similarity with such environmental, and more particularly, homologous proteins can be evaluated for cross reactivity with antibodies or T cell specific for such proteins. In a specific embodiment, the cross reactivity of vespid venom phospholipase $A_1$s with human lipases can be evaluated.

5.6. Therapeutic and Diagnostic uses of the Vespid Venom Phospholipase or Fragments Derivatives of Anologs Thereof The present invention provides a plentiful source of pure vespid venom phospholipase, or fragments, derivatives or analogs thereof, produced by recombinant techniques. Alternatively, given the sequence information provided by the present invention, polypeptide fragments, derivatives or analogs of the vespid venom phospholipases can be advantageously be produced by peptide synthesis.

The invention contemplates use of vespid venom phospholipases, or immunomodulatory fragments, derivatives or analogs thereof for the preparation of diagnostic or therapeutic compositions, for the use in the diagnosis and therapy of vespid venom allergen-specific allergic conditions. In particular, vespid phospholipase $A_1$, more particularly *Dolichovespula maculata* (white-face hornet) phospholipase $A_1$ (Dol m I) and *Vespula vulgaris* (yellowjacket) phospholipase $A_1$ (Ves v I), or immunomodulatory fragments, derivatives or analogs thereof are contemplated for use in diagnosis and therapy according to the present invention.

5.6.1. Diagnostic Methods

As used herein, the term diagnostic includes in vitro and in vivo diagnostic assays. Generally, such assays are designed to measure the activity of IgE antibodies specific for a given allergen. Such diagnostic assays depend heavily on the availability of pure allergen. This is especially true for determining sensitivity to a specific allergen component of a vespid venom. In vitro diagnostic assays for phospholipase sensitivity include radioimmunoassay (RIA), immunoradiometric immunoassay (IRMA), radio-allergosorbent tests (RAST), enzyme-linked immunosorbent assay (ELISA), ELISPOT, magnetic allergosorbent assay, immunoblots, histamine release assays, and the like.

The present invention further contemplates it vitro diagnostic assays on peripheral blood lymphocytes, as described in Section 5.5, supra. Such diagnostic assays can give detailed information about the phospholipase-specific T cell responses, the phenotype of the T cell response, and preferably the T cell epitope of the phospholipase involved in T cell responses. The immunodominant epitope and the epitope involved in IgE isotype class switch events can be detected, if they are not the same. In particular, the T cell epitopes of vespid venom phospholipases that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

In vivo assays for allergenicity generally consist of skin prick sensitivity assays, in which serially diluted amounts of an allergen are injected subcutaneously into a patient's skin, and wheel and erythema reactions are detected. As with in vitro assays, the availability of pure venom phospholipase greatly increases the value of the results of the in vivo diagnostic assays since cross-reactivity with impurities in extracts prepared from vespid venom sacs can be avoided.

5.6.2. Therapeutic Methods

Therapeutic compositions of the invention (see Section 5.6.3, infra) can be used in immunotherapy, also referred to as hyposensitization therapy. Immunotherapy has proven effective in allergic diseases, particular insect allergy. Allergens are administered parenterally over a long period of time in gradually increasing doses. Such therapy may be particularly effective when the allergen or allergens to which the patient is sensitive have been specifically identified and the therapy is targeted to those allergen(s). Thus, the availability of pure vespid venom phospholipase in large quantities is important for immunotherapy of allergy.

In another embodiment, the present invention contemplates use of polypeptides containing at least an immunomodulatory T cell epitope of a vespid venom phospholipase to induce specific T cell anergy to the vespid venom phospholipase. Identification of such peptides is described in Section 5.5, supra. Thus, a peptide comprising such a T cell epitope, particularly one lacking a B cell epitope, can be administered to a patient. Administration of such a peptide is expected to induce anergy, thus resulting in cessation of allergey-specific antibody production and a therapeutic effect.

In a preferred aspect of the invention, peptide based therapy to induce T cell anergy is customized for each individual or a group of individuals. Using the diagnostic methods of the present invention, the specific T cell epitope or epitopes of a vespid venom phospholipase involved in the allergic response can be identified. Peptides comprising these epitopes can then be used in an individualized immunotherapy regimen.

5.6.3. Pharmaceutically Acceptable Compositions

The in vivo diagnostic or therapeutic compositions of the invention may also contain appropriate pharmaceutically acceptable carriers, excipients, diluents and adjuvants. As used herein, the term "pharmaceutically acceptable" preferably means approved by a regulatory agency of a government, in particular the Federal government or a state government, or listed in the U.S. Pharmacopeia or another generally recognized pharmacopeia for use in animals, and more particularly in humans. Suitable pharmaceutical carriers are described in "Remington's Pharmaceutical Sciences" by E. W. Martin.

Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Such compositions will contain an effective diagnostic or therapeutic amount of the active compound together with a suitable amount of carrier so as to provide the form for proper administration to the patient. While intravenous injection is a very effective form of administration, other modes can be employed, such as by injection, or by oral, nasal or parenteral administration.

The invention will be further clarified by the following examples, which are intended to be purely exemplary of the invention.

6. EXAMPLE: VESPID VENOM PHOSPHOLIPASE $A_1$

The sequence of a venom allergen phospholipase $A_1$ from white-faced hornet (*Dolichovespula maculata*) by as been determined cDNA and protein sequencings. This protein of 300 amino acid residues (Dol m I) has no sequence similarity with other known phospholipases. However, it has sequence similarity with mammalian lipases; about 40% identity in overlaps of 123 residues. Hornet phospholipase was found to have weak lipase activity.

In a continuing effort to understand what immunochemical properties of a protein contribute to its allergenicity, the second major allergen of hornet venom cloned and sequenced. According to an accepted allergen nomenclature system (Marsh, et al., 1987, J. Allergy Clin. Immunol. 80:639), white-faced hornet phospholipase $A_1$ is designated Dol m I.

6.1. Materials and Methods 6.1.1. Isolation and Characterization of Dol m I and its CNBr Peptides Dol m I was isolated from venom sac extracts of white-faced hornet (Vespa Laboratory, Spring Mills, Pa.) as described (King, et al., 1985, J. Allergy and Clin. Immunol. 75:621). The protein (0.6 mg) was cleaved with CNBr (15 mg) in 75% $HCO_2H$ (0.2 ml) at 25° overnight. After cleavage the lyophilized mixture was separated on a Pep-RPC column (Pharmacia, Piscataway, N.J.) with a 2-propanol gradient of 0.1% per ml in 0.1% trifluoroacetic acid at a flow rate of 40 ml per hour. Selected fractions were rechromatographed under the same conditions after reduction and S-carboxymethylation (Fang, et al., 1988, Proc. Natl. Acad. Sci., USA. 85:895). The recovered peptides were characterized by Edman degradation on an Applied Biosystems gas phase sequencer.

6.1.2. Dol m I-Specific cDNA

Total RNAs were isolated from the acid gland of white-faced hornet using the guanidine thiocyanate extraction procedure (Fang, et al., 1988, supra). Dol m I-specific cDNA was obtained from total RNAs by the procedure of Frohman (Frohman, 1990, Amplifications: A Forum for PCR Users, 5:11; Frohman, et al., 1988, Proc. Natl. Acad. Sci. USA. 85:8998–9002) for rapid amplification of 3' or 5' cDNA ends (RACE).

First strand cDNAs were prepared using MeHgOH (Invitrogen, San Diego, Calif.) denatured total RNAs ($6\mu$) as the template and other reagents of a cDNA synthesis kit from GMCO-BRL (Gaithersburg, Md.) and RNasin (Promega Biotech) in a total reaction volume of 37 $\mu$l. For 5' RACE, the single strand cDNAs (from 6 $\mu$g of total RNAs) were poly-dA tailed with terminal deoxynucleotidyl transferase (US Biochemical, Cleveland, Ohio). The 3' or 5' RACE was carried out a with GenAmp PCR reagent kit (Perkin-Elmer Cetus, Norwalk, Conn.) using AmpliTaq polymerase, and 3' RACE was also made with Vent polymerase (New England Biolabs, Beverly, Mass.). For first round PCR, $\frac{1}{100}$ of the first strand cDNAs were used as a template. For the second round PCR, $\frac{1}{1000}$ of the first round PCR products were used as a template.

PCR products were examined by electrophoresis in 1.5% agarose gel with ethidium bromide staining and by Southern blot analysis. DNA was transferred to nitrocellulose membrane (Schleicher & Schuell, Keene, N.H.) and then was immobilized by UV cross-linking. Membranes were soaked for 2 hrs at 42° C. in a prehybridization solution of 30% formamide, 6×SSPE (Sambrook, et al., 1989, Molecular Cloning. Vol. 1 and 2, Cold Spring Harbor Laboratory Press), 5×Denhardt's solution (Sambrook, et al., 1989, supra), 100 $\mu$g/ml salmon sperm DNA, 0.1% SDS, and then hybridized overnight at 42° C. with $^{32}$P-labeled oligonucleotide probe ($1\times10^6$ cpm per ml of prehybridization solution). Post hybridization membranes were twice washed for 20 min at 60° in a solution of 3 M tetramethylammonium chloride, 0.2% SDS and 0.05 M Tris-HCl, pH 8.0 (Wood, et al., 1985, Proc. Natl. Acad. Sci. USA. 82:1585–1588). Oligonucleotides of specific activity $5\times10^7$ to $10^8$ cpm/$\mu$g were labeled with $\gamma$-$^{32}$P-ATP (New England Nuclear Corp) in presence of T4 polynucleotide kinase (New England Biolabs). The labeling procedure as well as other molecular biology procedures were taken from Sambrook, et al. (1989, supra).

PCR products contain single 3'-overhanging A-nucleotides (Clark, 1988, Nucl. Acids Res. 16:9677–9686) and were used directly for cloning into the PCR vector with compatible T-nucleotide overhangs (Invitrogen Corp, San Diego, Calif.). Plasmed DNAs were isolated from appropriate clones using the QIAGEN plasmid kit (QIAGEN, Chatworth, Calif.). DNA sequences were determined by the dideoxynucleotide chain-termination method (Sanger, et al., 1977, Proc. Natl. Acad. Sci. 74:5463–5467) using alkaline denatured plasmid DNAs and the Sequenase version 2.0 kit (US Biochemical, Cleveland, Ohio).

6.1.3. Phospholipase and Lipase Assays

Phospholipase activity was measured titrimetrically at 25±1° and pH 8 with 10% egg yolk as substrate in 0.2 N NaCl containing 0.5% Triton (King, et al., 1984, Arch. Biochem. Biophys. 230:1). Lipase activity was measured similarly using emulsions of 2% synthetic triglycerides triacetin, tributyrin, tricaprylin, triolein or tristearin (Sigma Biochemical, St. Louis, Mo.) as substrates.

6.2. Results
6.2.1. Partial Amino Acid Sequence of Dol m I

Partial amino acid sequence data were obtained from CNBr peptides. The partial or complete sequences of seven of these peptides correspond to residue 1–12, 14–30, 32–57, 85–96, 98–112, 161–170, 183–194 and 244–251 of the molecule shown in FIG. 1. The first five peptides correspond to the expected cleavage as in each case either preceded or terminated with a methionine residue. The last three peptides represent side products from acid cleavage of glutamyl peptide bonds. These partial amino acid sequence data were used for the design and synthesis of oligonucleotides SEQ ID NOS. 5, 6, 9 and 11 in Table 1.

the RACE procedure as outlined in FIG. 2A. Single stranded venom cDNAs were synthesized from total RNAs using a dT primer with $R_i+R_o$ adapter (oligonucleotide SEQ ID. NO: 1 in Table 1). Double stranded Dol m I-specific cDNA was amplified from single stranded venom cDNAs by two successive rounds of PCR using the nested primers as indicated. Several PCR products were detected and a major band of about 1 kb (FIG. 3) appeared to be the expected product when tested on Southern blot by hybridization with oligonucleotide SEQ ID NO: 9 (Table 1). As shown in FIG. 3, the 1 kb band was only found when Taq polymerase was used and it was not found with Vent polymerase.

The PCR products which contain the 1 kb band were cloned directly into plasmids. After transformation into bacteria, plasmids from 3 colonies were selected and sequenced. Two colonies have the nucleotide sequence of 115 to 1050 in FIG. 1 (SEQ ID. NO: 16). One of them differs from that shown by the deletion of one adenine base at position 968, and by the insertion of an additional 99 nucleotides at position 1027 in the 3'-untranslated region. A third colony differs from that shown at position 807 (C to T substitution; both encoding serine) and at position 812 (A to G substitution; asparagine to serine change).

TABLE 1

Oligonucleotides used as primers or probes for cloning hornet phospholipase

| SEQ ID. No. | Oligonucleotide* | Comment |
|---|---|---|
| 1 | AAG GAT CCG TCG ACA TCG ATA ATA CGA CTC ACT ATA GGG ATT $T_{15}$ | $(dT)_{17}$ $R_iR_o$ primer for first strand cDNA synthesis of 3' RACE. |
| 2 | AAG GAT CCG TCG ACA TC | $R_o$ anti-sense primer for first round PCR of 3' RACE. |
| 3 | GAC ATC GAT AAT ACG AC | $R_i$ anti-sense primer for second round PCR of 3' RACE. |
| 4 | $D^9$ T V K M $I^{14}$ | Sense primer for first round |
| 5 | GAY ACI GTI AAR ATG AT | PCR of 3' RACE. |
| 6 | $?K^{22}$ H D F Y $T^{27}$ | Sense primer for second |
| 7 | AAR CAY GAY TTY TAY AC | round PCR of 3' RACE. |
| 8 | $I^{190}$ Q V Y H A $D^{184}$ | Hybridization probe of |
| 9 | AT YTG IAC RTA RTG IGC RTC | PCR produce of 3' RACE; or primer for first strand cDNA synthesis of 5' RACE. |
| 10 | $P^{92}$ Y E D T $C^{87}$ | Anti-sense primer for first |
| 11 | GG RTA YTC RTC IGT RCA | round PCR of 5' RACE. |
| 12 | $M^{70}$ L A E $S^{66}$ | Anti-sense primer for |
| 13 | G CAT AAG AGC CTC TGA C | second round PCR of 5' RACE. |
| 14 | $M^{31}$ T D L $T^{27}$ | Hybridization probe for |
| 15 | T CAT TGT ATC TAG CGT A | PCR product of 5' RACE. |

*R represents A or G; Y represents C or T; I represents inosine.

6.2.2. cDNA Sequence of Dol m I.

cDNA encoding amino acid residues 22 to 300 and its 3'-untranslated region was amplified from venom RNAs by Using the cDNA data of FIG. 1, oligonucleotides of SEQ ID NOS. 13 and 15 in Table 1 were synthesized for amplifying the cDNA region which is 5' of nucleotide 115 in FIG.

1. As shown schematically in FIG. 2B, single stranded Dol m I-specific cDNA was synthesized from total RNAs using oligonucleotide SEQ ID NO: 9 as the primer, then poly-dA tailed with terminal deoxynucleotidyl transferase. Double-stranded Dol m I-specific cDNA was amplified from poly-da tailed specific cDNA by two successive rounds of PCR with the indicated primers. Several products formed after the second round of amplification and two bands of about 0.32 and 0.25 kbp (FIG. 3) appeared to be the expected products when detected on Southern blot by hybridization with oligonucleotide SEQ ID NO: 15 in Table 1. Following cloning into a plasmid, the product of 0.32 kbp was established to contain the cDNA sequence from nucleotide 1 to 262 in FIG. 1.

The region preceding nucleotide position 52 in FIG. 1 encodes a leader sequence of 17 amino acid residues as the N-teminal amino acid residue of Dol m I. The Dol m I protein was found on Edman degradation to begin at nucleotide position 52. The protein sequence suggests the presence of two possible glycosylation sites at residue 8 and 212. The site at residue 8 is probably glycosylated as repeated attempts to identify this residue by Edman degradation gave negative results. The presence of a carboyhydrate on the Dol m I protein is also suggested by the difference in the molecular weight of 33,745, calculated from the deduced sequence, and the observed molecular weight of about 37,000, estimated from SDS gel electrophoresis.

6.2.3. Lipase Activity of Hornet Phospholipase

It has been reported previously (King et al., 1985, J. Allergy Clin. Immunol. 75:621–628) that vespid phospholipase catalyzes a rapid hydrolysis of the acyl group at position 1 of synthetic phosphatidylcholines and slow hydrolysis of the acyl group at position 2. Therefore, vespid phospholipases have both $A_1$ and B types of phospholipase activites. The present finding on sequence similarity of hornet phospholipase with lipases prompted tests for lipase activity.

The enzyme sample tested had about 280 units of phospholipase activity per mg when tested with egg yolk as a substrate as compared to the previously reported specific activity of 1,100 units per mg (King, et al., 1985, supra) and its low specific activity was due to inadvertent prolonged exposure to low pH. This sample had lipase activities of 13 and 33 (±20%) units/mg with triacetin and tributyrin, respectively, as substrates. These data indicate that hornet phospholipase has a weak lispase activity.

6.3. Discussion

Sequence comparison by the FASTA method (Pearson and Lipman, 1988, Proc. Natl. Acad. Sci. USA 85:2444) showed that Dol m I has no similarity with other known phospholipases in the literature, but it has similarity with mammalian lipases. This is shown in FIG. 4 for lipoprotein lipases and hepatic lipases from human and mouse (Kirchgessner, et al., 10 1987, J. Biol. Chem. 262:8463; Oka, et al., 1991, Biochim. Biophys. Acta. 1089:13). Human pancreatic lipase (Winkler, et al., 1990, Nature. 343:771) has about the same degree of similarity with Dol m I as human hepatic lipase. There is about 40% identity in overlaps of 123 residues of mammalian lipases and Dol m I. The sequence region of lipases shown in FIG. 4 is highly conserved as similar sequences are found for a number of other mammalian and prokaryotic lipases and a Drosophila protein vitellogenin (Persson, et al., 1989, Eur. J. Biochem. 179:39; Bownes, et al., 1988, Proc. Natl. Acad. Sci. USA. 85:1554). Thus these proteins also have significant sequence similarity with Dol m I.

The most strongly conserved region of all lipases is reported to be in the undecapeptide region of residue 153–163 of human lipoprotein lipase (Persson, et al., 1989, supra). This region is believed to be of importance for lipase activity, and it is the region of highest identity of lipases and Dol m I. Interestingly Dol m I does have weak lipase activity with synthetic triglycerides.

All vespid allergic patients invariably have antibodies specific for both Dol m I and V. Therefore we compared the sequences of these two proteins and they are found to share one similar octapeptide sequence: VNRHNQFR (SEQ ID NO: 23) and LKRHNDFR (SEQ IN NO: 24) at position 45–52 of Dol m VA and B respectively, and MNRHNEFK (SEQ ID NO: 25) at position 31–38 of Dol m I. However, this octapeptide sequence is not in the sequence region where these allergens show similarity with other proteins.

There are several examples of sequence similarity of allergens with other proteins in our environment. Some examples are: birch pollen allergen Bet v I with a pea disease resistance response gene (Breiteneder, et al., 1989, EMBO J. 8:1935); Bet v II and its homologs from timothy and mugwort pollens with human profilin (Valenta, et al., 1992, J. Exp. Med. 175:377); mite allergen Der p I with human cathepsin and other cysteine proteases (Chua, et al., 1988, J. Exp. Med. 167:175); bee venom allergen phospholipase $A_2$ with human pancreatic enzyme; and bee venom allergen melittin Api m III with human complement C9 (Cf. King et al., 1990, Protein Sequences and Data Analysis 3:263). However, several other major allergens from mite (Chua, et al., 1990, Int. Arch, Allergy Appl. Immunol. 91:124; Tovey, et al., 1989, J. Exp. Med. 170:1457) and ragweed and grass pollens (Rafnar, et al., 1991, J. Biol. Chem. 266:1229; Rogers, et al., 1991, J. Immunol. 147:2547; Silvavovich, et al., 1991, J. Biol. Chem. 266:1204; Singh, et al., 1991, Proc. Natl. Acad. Sci. 88:1384) have no known sequence similarity with other proteins in our environment.

It is a great advantage, therefore, that the gene encoding a vespid phospholipase, Dol m I, has been cloned and sequenced, since recombinant expression of the vespid phospholipase should provide an ample source of protein for testing cross-reactivity and for determination of the relevant B cell and T cell epitopes.

7. YELLOWJACKET PHOSPHOLIPASE $A_1$

Using the procedures described in Section 6, supra, the cDNA sequence for yellowjacket (*Vespula vulgaris*) phosse $A_1$ (Ves v I) was obtained. The complete cDNA sequence and deduced amino acid sequence of Ves v I are shown in FIG. 5 and in SEQ ID NOS: 26 and 27, respectively.

The sequence analysis described in Section 6–3, supra, was performed on the sequence shown in FIG. 5. Notably, this sequence is identical to that of Dol m I at about ⅔ of the residues. Like Dol m I, Ves v I has about 40% identity in overlaps of 123 residues of mammalian lipases (see FIG. 4). This identity of segments of Ves v I with mammalian lipases is believed to have significance in allergy.

8. DEPOSIT OF MICROORGANISMS

A bacterial strain INFαF' containing a recombinant plasmid pCR which has a nucleic acids encoding white face hornet phospholipase, $A_1$ designated WFH-PLA, has been deposited on Mar. 11, 1993 with the American Type Culture Collection (ATCC), 12301 Parklawn Drive, Rockville, Md. 20852, under the provisions of the Budapest Treaty on the International Recoghition of the Deposit of Microorganisms for the Purposes of Patent Procedures, and has been assigned ATCC accession number 69254.

The present invention is not to be limited in scope by the microorganisms deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

What is claimed is:

1. A vespid venom phosphoripase fusion protein comprising an immunomodulatory polypeptide fragment of a vespid venom phospholipase encoded by a nucleic acid of SEQ ID NO:16 or SEQ ID NO:26.

2. The fusion protein according to claim 1, wherein the fusion protein further comprises a polyhistidine polypeptide.

3. The fusion protein according to claim 1, wherein the vespid venom phospholipase is from a vespid of a genus Dolichovespula.

4. The fusion protein according to claim 3, wherein the vespid venom phospholipase is from a species *maculata*.

5. The fusion protein according to claim 4, wherein the vespid venom phospholipase has an amino acid sequence as depicted in SEQ ID NO:17.

6. The fusion protein according to claim 4, wherein the vespid venom phospholipase comprises an amino acid sequence as depicted in SEQ ID NO:22.

7. The fusion protein according to claim 1, wherein the vespid venom phospholipase is from a vespid of a genus Vespula.

8. The fusion protein according to claim 7, wherein the vespid venom phospholipase is from a species *vulgaris*.

9. The fusion protein according to claim 8, wherein the vespid venom phospholipase has an amino acid sequence as depicted in SEQ ID NO:27.

10. A method of preparing a composition comprising mixing the fusion protein of claim 1 with a pharmaceutically acceptable carrier.

11. A composition comprising the fusion protein of claim 1 and a pharmaceutically acceptable carrier.

12. A method for treating a vespid venom allergen-specific allergic condition comprising administering a therapeutically effective dose of the fusion protein of claim 1 to a subject suffering from the allergic condition.

* * * * *

UNITED STATES PATENT AND TRADEMARK OFFICE
CERTIFICATE OF CORRECTION

PATENT NO.     : 6,270,763 B1
DATED          : August 7, 2001
INVENTOR(S)    : Te Piao King It is certified that error appears in the above-identified patent and that said Letters Patent is hereby corrected as shown below:

Title page,
Item [54], in the second line of the title, please correct "VENUM" to -- VENOM --.

Item [76], Inventor and before item [*] Notice, on a separate line, please list the assignee as
-- The Rockefeller University, New York, NY (US) --.

Signed and Sealed this

Twenty-sixth Day of March, 2002

*Attest:*

JAMES E. ROGAN
*Attesting Officer*       *Director of the United States Patent and Trademark Office*

```
                          SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

AAGGATCCGT CGACATCGAT AATACGACTC ACTATAGGGA TTT                 43

(2) INFORMATION FOR SEQ ID NO:2:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

AAGGATCCGT CGACATC                                              17

(2) INFORMATION FOR SEQ ID NO:3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:3:

GACATCGATA ATACGAC                                              17

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Asp Thr Val Lys Met Ile
1               5
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GAYACNGTNA ARATGAT                                  17

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Lys His Asp Phe Tyr Thr
1             5

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AARCAYGAYT TYTAYAC                                  17

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ile Gln Val Tyr His Ala Asp
1             5

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ATYTGNACRT ARTGNGCRTC                              20

(2) INFORMATION FOR SEQ ID NO:10:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:10:

```
Pro Tyr Glu Asp Thr Cys
1               5
```

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
GGRTAYTCRT CNGTRCA                                              17
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Met Leu Ala Glu Ser
1               5
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
GCATAAGAGC CTCTGAC                                              17
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Thr Asp Leu Thr
1               5
```

(2) INFORMATION FOR SEQ ID NO:15:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:15:

TCATTGTATC TAGCGTA                                                       17

(2) INFORMATION FOR SEQ ID NO:16:

(i) SEQUENCE CHARACTERISTICS:
        (A) LENGTH: 1050 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..951

(xi) SEQUENCE DESCRIPTION: SEQ ID NO:16:

```
AGA TTA ATA ATG TTC GTA GGT GAT CCG TCG TCA TCA AAT GAA TTA GAT        48
Arg Leu Ile Met Phe Val Gly Asp Pro Ser Ser Ser Asn Glu Leu Asp
 1               5                  10                  15

AGA TTC TCC GTA TGT CCC TTT AGT AAT GAT ACA GTT AAG ATG ATT TTT        96
Arg Phe Ser Val Cys Pro Phe Ser Asn Asp Thr Val Lys Met Ile Phe
             20                  25                  30

TTA ACA AGG GAA AAC CGA AAA CAT GAT TTT TAT ACG CTA GAT ACA ATG       144
Leu Thr Arg Glu Asn Arg Lys His Asp Phe Tyr Thr Leu Asp Thr Met
         35                  40                  45

AAC AGG CAC AAT GAA TTT AAG AAG TCA ATC ATA AAA CGT CCA GTT GTA       192
Asn Arg His Asn Glu Phe Lys Lys Ser Ile Ile Lys Arg Pro Val Val
     50                  55                  60

TTC ATT ACG CAT GGT TTT ACT TCG TCT GCA ACC GAA AAA AAT TTC GTT       240
Phe Ile Thr His Gly Phe Thr Ser Ser Ala Thr Glu Lys Asn Phe Val
 65                  70                  75                  80

GCT ATG TCA GAG GCT CTT ATG CAT ACA GGT GAT TTT CTT ATA ATT ATG       288
Ala Met Ser Glu Ala Leu Met His Thr Gly Asp Phe Leu Ile Ile Met
                 85                  90                  95

GTC GAT TGG CGG ATG GCT GCT TGT ACT GAT GAA TAC CCA GGT CTG AAG       336
Val Asp Trp Arg Met Ala Ala Cys Thr Asp Glu Tyr Pro Gly Leu Lys
            100                 105                 110

TAT ATG TTT TAT AAG GCT GCC GTT GGT AAT ACA CGC TTA GTT GGA AAT       384
Tyr Met Phe Tyr Lys Ala Ala Val Gly Asn Thr Arg Leu Val Gly Asn
        115                 120                 125

TTT ATC GCT ATG ATC GCA AAG AAA CTT GTA GAA CAA TAT AAA GTG CCG       432
Phe Ile Ala Met Ile Ala Lys Lys Leu Val Glu Gln Tyr Lys Val Pro
    130                 135                 140

ATG ACA AAT ATA CGA CTG GTG GGA CAC AGT TTG GGC GCA CAC ATT TCA       480
Met Thr Asn Ile Arg Leu Val Gly His Ser Leu Gly Ala His Ile Ser
145                 150                 155                 160

GGT TTC GCA GGC AAA AGA GTT CAA GAG TTA AAA TTA GGA AAA TTT TCT       528
Gly Phe Ala Gly Lys Arg Val Gln Glu Leu Lys Leu Gly Lys Phe Ser
                165                 170                 175

GAA ATT ATT GGG CTT GAT CCT GCT GGG CCT AGT TTC AAG AAA AAT GAT       576
Glu Ile Ile Gly Leu Asp Pro Ala Gly Pro Ser Phe Lys Lys Asn Asp
            180                 185                 190

TGT TCC GAG AGA ATC TGC GAG ACA GAC GCA CAT TAT GTA CAA ATT TTA       624
Cys Ser Glu Arg Ile Cys Glu Thr Asp Ala His Tyr Val Gln Ile Leu
```

-continued

```
                195                     200                     205
CAT ACA TCG AGC AAT TTA GGA ACA GAG AGA ACT CTT GGC ACC GTC GAT       672
His Thr Ser Ser Asn Leu Gly Thr Glu Arg Thr Leu Gly Thr Val Asp
        210                     215                     220

TTC TAC ATA AAT AAC GGA AGT AAT CAA CCC GGT TGC AGA TAT ATT ATT       720
Phe Tyr Ile Asn Asn Gly Ser Asn Gln Pro Gly Cys Arg Tyr Ile Ile
225                     230                     235                 240

GGA GAA ACT TGC TCT CAT ACG AGA GCC GTG AAA TAC TTT ACC GAG TGC       768
Gly Glu Thr Cys Ser His Thr Arg Ala Val Lys Tyr Phe Thr Glu Cys
                    245                     250                     255

ATA AGA CGC GAA TGT TGT TTA ATT GGG GTC CCG CAG TCC AAG AAT CCG       816
Ile Arg Arg Glu Cys Cys Leu Ile Gly Val Pro Gln Ser Lys Asn Pro
            260                     265                     270

CAG CCT GTT TCG AAG TGC ACA AGA AAC GAG TGC GTT TGC GTT GGA TTA       864
Gln Pro Val Ser Lys Cys Thr Arg Asn Glu Cys Val Cys Val Gly Leu
        275                     280                     285

AAC GCA AAG AAA TAT CCT AAA AGG GGC TCA TTT TAT GTA CCG GTT GAA       912
Asn Ala Lys Lys Tyr Pro Lys Arg Gly Ser Phe Tyr Val Pro Val Glu
290                     295                     300

GCT GAA GCT CCA TAT TGC AAT AAC AAC GGG AAA ATA ATT TAATTATATA        961
Ala Glu Ala Pro Tyr Cys Asn Asn Asn Gly Lys Ile Ile
305                     310                     315

AAAAAAACAT TACTATTGAC ACAAGTGCAT TTGTTAATGA TGAAATGAAT AAATTACGAT    1021

TCAAGAAAAA AAAAAAAAAA AAAAAAAA                                      1050
```

(2) INFORMATION FOR SEQ ID NO:17:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:17:

```
Arg Leu Ile Met Phe Val Gly Asp Pro Ser Ser Asn Glu Leu Asp
1               5                   10                  15

Arg Phe Ser Val Cys Pro Phe Ser Asn Asp Thr Val Lys Met Ile Phe
            20                  25                  30

Leu Thr Arg Glu Asn Arg Lys His Asp Phe Tyr Thr Leu Asp Thr Met
        35                  40                  45

Asn Arg His Asn Glu Phe Lys Lys Ser Ile Ile Lys Arg Pro Val Val
    50                  55                  60

Phe Ile Thr His Gly Phe Thr Ser Ser Ala Thr Glu Lys Asn Phe Val
65                  70                  75                  80

Ala Met Ser Glu Ala Leu Met His Thr Gly Asp Phe Leu Ile Ile Met
                85                  90                  95

Val Asp Trp Arg Met Ala Ala Cys Thr Asp Glu Tyr Pro Gly Leu Lys
            100                 105                 110

Tyr Met Phe Tyr Lys Ala Ala Val Gly Asn Thr Arg Leu Val Gly Asn
        115                 120                 125

Phe Ile Ala Met Ile Ala Lys Lys Leu Val Glu Gln Tyr Lys Val Pro
    130                 135                 140

Met Thr Asn Ile Arg Leu Val Gly His Ser Leu Gly Ala His Ile Ser
145                 150                 155                 160

Gly Phe Ala Gly Lys Arg Val Gln Glu Leu Lys Leu Gly Lys Phe Ser
                165                 170                 175
```

```
Glu Ile Ile Gly Leu Asp Pro Ala Gly Pro Ser Phe Lys Lys Asn Asp
            180                 185                 190

Cys Ser Glu Arg Ile Cys Glu Thr Asp Ala His Tyr Val Gln Ile Leu
            195                 200                 205

His Thr Ser Ser Asn Leu Gly Thr Glu Arg Thr Leu Gly Thr Val Asp
            210                 215                 220

Phe Tyr Ile Asn Asn Gly Ser Asn Gln Pro Gly Cys Arg Tyr Ile Ile
225                 230                 235                 240

Gly Glu Thr Cys Ser His Thr Arg Ala Val Lys Tyr Phe Thr Glu Cys
            245                 250                 255

Ile Arg Arg Glu Cys Cys Leu Ile Gly Val Pro Gln Ser Lys Asn Pro
            260                 265                 270

Gln Pro Val Ser Lys Cys Thr Arg Asn Glu Cys Val Cys Val Gly Leu
            275                 280                 285

Asn Ala Lys Lys Tyr Pro Lys Arg Gly Ser Phe Tyr Val Pro Val Glu
            290                 295                 300

Ala Glu Ala Pro Tyr Cys Asn Asn Asn Gly Lys Ile Ile
305                 310                 315
```

(2) INFORMATION FOR SEQ ID NO:18:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Tyr Pro Val Ser Ala Gly Tyr Thr Lys Leu Val Gly Gln Asp Val Ala
1                   5                   10                  15

Arg Phe Ile Asn Trp Met Glu Glu Phe Asn Tyr Pro Leu Asp Asn
            20                  25                  30

Val His Leu Leu Gly Tyr Ser Leu Gly Ala His Ala Ala Gly Ile Ala
            35                  40                  45

Gly Ser Leu Thr Asn Lys Lys Val Asn Arg Ile Thr Gly Leu Asp Pro
50                  55                  60

Ala Gly Pro Asn Phe Glu Tyr Ala Glu Ala Pro Ser Arg Leu Ser Pro
65                  70                  75                  80

Asp Asp Ala Asp Phe Val Asp Val Leu His Thr Phe Thr Arg Gly Ser
            85                  90                  95

Pro Gly Arg Ser Ile Gly Ile Gln Lys Pro Val Gly His Val Asp Ile
            100                 105                 110

Tyr Pro Asn Gly Gly Thr Phe Gln Pro Gly Cys
            115                 120
```

(2) INFORMATION FOR SEQ ID NO:19:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Tyr Pro Val Ser Ala Gly Tyr Thr Lys Leu Val Gly Asn Asp Val Ala
1                   5                   10                  15
```

```
Arg Phe Ile Asn Trp Met Glu Glu Phe Asn Tyr Pro Leu Asp Asn
             20                  25                  30

Val His Leu Leu Gly Tyr Ser Leu Gly Ala His Ala Ala Gly Val Ala
             35                  40                  45

Gly Ser Leu Thr Asn Lys Lys Val Asn Arg Ile Thr Gly Leu Asp Pro
 50                  55                  60

Ala Gly Pro Asn Phe Glu Tyr Ala Glu Ala Pro Ser Arg Leu Ser Pro
 65                  70                  75                  80

Asp Asp Ala Asp Phe Val Asp Val Leu His Thr Phe Thr Arg Gly Ser
                 85                  90                  95

Pro Gly Arg Ser Ile Gly Ile Gln Lys Pro Val Gly His Val Asp Ile
            100                 105                 110

Tyr Pro Asn Gly Gly Thr Phe Gln Pro Gly Cys
            115                 120

(2) INFORMATION FOR SEQ ID NO:20:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Tyr Thr Ile Ala Val Arg Asn Thr Arg Leu Val Gly Lys Glu Val Ala
 1               5                  10                  15

Ala Leu Leu Arg Trp Leu Glu Glu Ser Val Gln Leu Ser Arg Ser His
             20                  25                  30

Val His Leu Ile Gly Tyr Ser Leu Gly Ala His Val Ser Gly Phe Ala
             35                  40                  45

Gly Ser Ser Ile Gly Gly Thr His Lys Ile Gly Arg Ile Thr Gly Leu
 50                  55                  60

Asp Ala Ala Gly Pro Leu Phe Glu Gly Ser Ala Pro Ser Asn Arg Leu
 65                  70                  75                  80

Ser Pro Asp Asp Ala Asn Phe Val Asp Ala Ile His Thr Phe Thr Arg
                 85                  90                  95

Glu His Met Gly Leu Ser Val Gly Ile Lys Gln Pro Ile Gly His Tyr
            100                 105                 110

Asp Phe Tyr Pro Asn Gly Gly Ser Phe Gln Pro Gly Cys
            115                 120                 125

(2) INFORMATION FOR SEQ ID NO:21:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Tyr Thr Gln Ala Ser Tyr Asn Thr Arg Val Leu Gly Ala Glu Ile Ala
 1               5                  10                  15

Phe Leu Val Gln Val Leu Ser Thr Glu Met Gly Tyr Ser Pro Glu Asn
             20                  25                  30

Val His Leu Ile Pro His Ser Leu Gly Ser His Val Ala Gly Glu Ala
```

```
                    35                  40                  45
Gly Arg Arg Leu Glu Gly His Val Gly Arg Ile Thr Gly Leu Asp Pro
            50                  55                  60
Ala Glu Pro Cys Phe Gln Gly Leu Pro Glu Glu Val Arg Leu Asp Pro
65                  70                  75                  80
Ser Asp Ala Met Phe Val Asp Val Ile His Thr Asp Ser Ala Pro Ile
                85                  90                  95
Ile Pro Tyr Leu Gly Phe Gly Met Ser Gln Lys Val Gly His Leu Asp
            100                 105                 110
Phe Phe Pro Asn Gly Gly Lys Glu Ile Pro Gly Cys
            115                 120
```

(2) INFORMATION FOR SEQ ID NO:22:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Tyr Lys Ala Ala Val Gly Asn Thr Arg Leu Val Gly Asn Phe Ile Ala
1                   5                   10                  15
Met Ile Ala Lys Lys Leu Val Glu Gln Tyr Lys Val Pro Met Thr Asn
            20                  25                  30
Ile Arg Leu Val Gly His Ser Leu Gly Ala His Ile Ser Gly Phe Ala
            35                  40                  45
Gly Lys Arg Val Gln Glu Leu Lys Leu Gly Lys Phe Ser Glu Ile Ile
            50                  55                  60
Gly Leu Asp Pro Ala Gly Pro Ser Phe Lys Lys Asn Asp Cys Ser Glu
65                  70                  75                  80
Arg Ile Cys Glu Thr Asp Ala His Tyr Val Gln Ile Leu His Thr Ser
                85                  90                  95
Ser Asn Leu Gly Thr Glu Arg Thr Leu Gly Thr Val Asp Phe Tyr Ile
            100                 105                 110
Asn Asn Gly Ser Asn Gln Pro Gly Cys
            115                 120
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Val Asn Arg His Asn Gln Phe Arg
1                   5
```

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Leu Lys Arg His Asn Asp Phe Arg
1               5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Met Asn Arg His Asn Glu Phe Lys
1               5
```

(2) INFORMATION FOR SEQ ID NO:26:

(i) SEQUENCE CHARACTERISTICS:
        (A) LENGTH: 1341 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 153..1052

(xi) SEQUENCE DESCRIPTION: SEQ ID NO:26:

```
ATTTCCGGGT AAGTTTGTGT ACGTTTCTAC ACAAAACAAA AATCATGGAA GAAAATATGA      60

ATTTAAAGTA TTTATTATTA TTCGTGTATT TTGTGCAAGT GTTAAATTGT TGCTATGGAC     120

ATGGTGATCC GTTATCTTAC GAATTAGATA GA GGA CCC AAA TGT CCT TTT AAT      173
                                Gly Pro Lys Cys Pro Phe Asn
                                  1               5

TCT GAT ACA GTT TCG ATA ATT ATT GAA ACA AGG GAA AAC CGA AAT CGT      221
Ser Asp Thr Val Ser Ile Ile Ile Glu Thr Arg Glu Asn Arg Asn Arg
         10              15                  20

GAT CTT TAT ACA CTA CAG ACA TTA CAG AAT CAT CCT GAA TTT AAG AAA      269
Asp Leu Tyr Thr Leu Gln Thr Leu Gln Asn His Pro Glu Phe Lys Lys
     25                  30                  35

AAA ACT ATA ACA CGT CCA GTT GTA TTC ATT ACA CAT GGT TTT ACT TCA      317
Lys Thr Ile Thr Arg Pro Val Val Phe Ile Thr His Gly Phe Thr Ser
 40              45                  50                  55

TCT GCA AGT GAA ACA AAT TTC ATA AAT TTA GCA AAA GCT TTG GTA GAT      365
Ser Ala Ser Glu Thr Asn Phe Ile Asn Leu Ala Lys Ala Leu Val Asp
             60                  65                  70

AAA GAT AAC TAT ATG GTT ATC TCA ATC GAT TGG CAG ACG GCT GCT TGT      413
Lys Asp Asn Tyr Met Val Ile Ser Ile Asp Trp Gln Thr Ala Ala Cys
                 75                  80                  85

ACT AAT GAA GCT GCA GGT TTA AAG TAT TTA TAT TAT CCT ACT GCT GCT      461
Thr Asn Glu Ala Ala Gly Leu Lys Tyr Leu Tyr Tyr Pro Thr Ala Ala
                     90                  95                 100

AGA AAT ACA CGT TTA GTT GGA CAA TAT ATC GCT ACG ATT ACC CAG AAA      509
Arg Asn Thr Arg Leu Val Gly Gln Tyr Ile Ala Thr Ile Thr Gln Lys
            105                 110                 115

CTC GTA AAA CAC TAT AAA ATC TCG ATG GCA AAT ATA CGA TTA ATT GGA      557
Leu Val Lys His Tyr Lys Ile Ser Met Ala Asn Ile Arg Leu Ile Gly
120                 125                 130                 135
```

-continued

```
CAT AGC TTA GGA GCA CAT GCT TCA GGT TTT GCA GGC AAA AAG GTT CAA      605
His Ser Leu Gly Ala His Ala Ser Gly Phe Ala Gly Lys Lys Val Gln
            140                 145                 150

GAG TTA AAA TTA GGA AAA TAT TCT GAA ATT ATT GGG CTT GAT CCT GCT      653
Glu Leu Lys Leu Gly Lys Tyr Ser Glu Ile Ile Gly Leu Asp Pro Ala
            155                 160                 165

AGG CCT TCG TTC GAT TCA AAT CAT TGT TCC GAA AGA CTC TGC GAG ACA      701
Arg Pro Ser Phe Asp Ser Asn His Cys Ser Glu Arg Leu Cys Glu Thr
            170                 175                 180

GAT GCA GAA TAT GTT CAA ATT ATA CAT ACA TCA AAC TAT TTA GGA ACC      749
Asp Ala Glu Tyr Val Gln Ile Ile His Thr Ser Asn Tyr Leu Gly Thr
185                 190                 195

GAA AAA ACC CTT GGT ACC GTC GAT TTC TAC ATG AAT AAC GGA AAG AAT      797
Glu Lys Thr Leu Gly Thr Val Asp Phe Tyr Met Asn Asn Gly Lys Asn
200                 205                 210                 215

CAA CCT GGT TGC GGT AGA TTT TTC TCA GAA GTT TGC TCT CAT TCG AGA      845
Gln Pro Gly Cys Gly Arg Phe Phe Ser Glu Val Cys Ser His Ser Arg
            220                 225                 230

GCC GTG ATA TAC ATG GCT GAG TGC ATA AAA CAC GAA TGT TGT TTA ATT      893
Ala Val Ile Tyr Met Ala Glu Cys Ile Lys His Glu Cys Cys Leu Ile
            235                 240                 245

GGG ATA CCG AAG TCA AAG AGT TCG CAG CCT ATT TCG TCG TGC ACA AAA      941
Gly Ile Pro Lys Ser Lys Ser Ser Gln Pro Ile Ser Ser Cys Thr Lys
            250                 255                 260

CAG GAG TGC GTT TGC GTT GGA TTA AAC GCA AAG AAG TAT ACT AGT AGA      989
Gln Glu Cys Val Cys Val Gly Leu Asn Ala Lys Lys Tyr Thr Ser Arg
            265                 270                 275

GGC TCA TTT TAT GTA CCG GTT GAA AGT ACT GTT CCT TTT TGC AAT AAC     1037
Gly Ser Phe Tyr Val Pro Val Glu Ser Thr Val Pro Phe Cys Asn Asn
280                 285                 290                 295

AAG GGG AAG ATA ATT TAATAATATA AAAAAGTAAT TCCATTCAT CGAAATGCAT      1092
Lys Gly Lys Ile Ile
                300

TTGTTAATGG TGAATGAATA AATTACCATT TAACAAATAA TCGTACATGC AGAATGTCGT   1152

CCAAAATAAT TGCGGAGTAT ATAATGGATG ATCTTAGCAA ATTTAAAAAA TAAAAGAAT    1212

TATATAAACA TATACCCTAT TTGATTTTGC TTTTTAGTTG TAGTGAATTG AATTTTTCTG   1272

TCTGCTTAAT TTGAAACTGC TTCCTTGCTT CTGAATAAAT GCCTGTAAAC ATAAAAAAAA   1332

AAAAAAAAA                                                          1341
```

(2) INFORMATION FOR SEQ ID NO:27:

(i) SEQUENCE CHARACTERISTICS:
        (A) LENGTH: 300 amino acids
        (B) TYPE: amino acid
        (D) TOPOLOGY: linear (ii) MOLECULE TYPE: protein (xi) SEQUENCE DESCRIPTION: SEQ ID NO:27:

```
Gly Pro Lys Cys Pro Phe Asn Ser Asp Thr Val Ser Ile Ile Glu
  1               5                  10                  15

Thr Arg Glu Asn Arg Asn Arg Asp Leu Tyr Thr Leu Gln Thr Leu Gln
                 20                  25                  30

Asn His Pro Glu Phe Lys Lys Lys Thr Ile Thr Arg Pro Val Val Phe
             35                  40                  45

Ile Thr His Gly Phe Thr Ser Ser Ala Ser Glu Thr Asn Phe Ile Asn
         50                  55                  60
```

-continued

```
Leu Ala Lys Ala Leu Val Asp Lys Asp Asn Tyr Met Val Ile Ser Ile
 65                  70                  75                  80

Asp Trp Gln Thr Ala Ala Cys Thr Asn Glu Ala Ala Gly Leu Lys Tyr
                 85                  90                  95

Leu Tyr Tyr Pro Thr Ala Ala Arg Asn Thr Arg Leu Val Gly Gln Tyr
            100                 105                 110

Ile Ala Thr Ile Thr Gln Lys Leu Val Lys His Tyr Lys Ile Ser Met
        115                 120                 125

Ala Asn Ile Arg Leu Ile Gly His Ser Leu Gly Ala His Ala Ser Gly
    130                 135                 140

Phe Ala Gly Lys Lys Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
            165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Thr Leu Gly Thr Val Asp Phe
        195                 200                 205

Tyr Met Asn Asn Gly Lys Asn Gln Pro Gly Cys Gly Arg Phe Phe Ser
    210                 215                 220

Glu Val Cys Ser His Ser Arg Ala Val Ile Tyr Met Ala Glu Cys Ile
225                 230                 235                 240

Lys His Glu Cys Cys Leu Ile Gly Ile Pro Lys Ser Lys Ser Ser Gln
            245                 250                 255

Pro Ile Ser Ser Cys Thr Lys Gln Glu Cys Val Cys Val Gly Leu Asn
            260                 265                 270

Ala Lys Lys Tyr Thr Ser Arg Gly Ser Phe Tyr Val Pro Val Glu Ser
        275                 280                 285

Thr Val Pro Phe Cys Asn Asn Lys Gly Lys Ile Ile
    290                 295                 300
```